United States Patent
Taron et al.

(10) Patent No.: US 10,260,056 B2
(45) Date of Patent: *Apr. 16, 2019

(54) CLEAVAGE OF FUCOSE IN N-GLYCANS

(71) Applicant: New England Biolabs, Inc., Ipswich, MA (US)

(72) Inventors: Christopher H. Taron, Essex, MA (US); Saulius Vainauskas, Newburyport, MA (US); Xiaofeng Shi, Beverly, MA (US)

(73) Assignee: New England Biolabs, Inc., Ipswich, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/894,252

(22) Filed: Feb. 12, 2018

(65) Prior Publication Data

US 2018/0265854 A1 Sep. 20, 2018

Related U.S. Application Data

(60) Provisional application No. 62/474,860, filed on Mar. 22, 2017, provisional application No. 62/472,994, filed on Mar. 17, 2017.

(51) Int. Cl.
*C12N 9/26* (2006.01)
*C07H 5/06* (2006.01)
(Continued)

(52) U.S. Cl.
CPC .......... *C12N 9/2402* (2013.01); *C07H 5/06* (2013.01); *C07K 1/13* (2013.01); *C12P 21/005* (2013.01);
(Continued)

(58) Field of Classification Search
None
See application file for complete search history.

(56) References Cited

U.S. PATENT DOCUMENTS

2012/0107942 A1  5/2012  Baginski
2015/0346194 A1  12/2015 Magnelli et al.
2017/0128554 A1* 5/2017  Chen .............. C12N 9/0006

FOREIGN PATENT DOCUMENTS

WO  WO2013/049622       4/2013
WO  WO2015/184008       12/2015
WO  WO-2016003795 A1 * 1/2016 ........... C12N 9/0006

OTHER PUBLICATIONS

Studer Residue mutations and their impact on protein structure and function: detecting beneficial and pathogenic changes. Residue mutations and their impact on protein structure and function: detecting beneficial and pathogenic changes. Biochem. J. (2013) 449, 581-594.*

(Continued)

*Primary Examiner* — Yong D Pak
(74) *Attorney, Agent, or Firm* — New England Biolabs, Inc; Harriet M. Strimpel

(57) ABSTRACT

Provided herein is an α-fucosidase that can cleave a conjugate comprising an N-glycan and a label where the label is added by amine reactive chemistry. The α-fucosidase also has an accelerated reaction time using Schiff base labeled N-glycans compared with bovine kidney fucosidase. A reaction mix, enzyme mix and kit comprising the α-fucosidase are provided, as well as a method for analyzing glycoproteins. The α-fucosidase finds particular use in analyzing the N-glycans of therapeutic glycoproteins.

17 Claims, 22 Drawing Sheets
(15 of 22 Drawing Sheet(s) Filed in Color)
Specification includes a Sequence Listing.

Alpha-L-fucosidase of Omnitrophica bacterium OLB16 (SEQ ID NO: 1):

```
  1 MRYILAVLLM VGMMAGAATA VTYEPTWESL DSRPNPAWFD EAKFGIFIHW GVYAVPAWGS
 61 KGKYSEWYWN DMMDPNGETW KFHLKTYGED FKYQDFAPMF KAEMFDPAQW ADIFARSGAK
121 YVVLTSKHHE GFCLWPSPDS WNWNSVDIGP HRDLCGDLTQ AVRDRGLKMG FYYSLYEWFN
181 PIYKTDVHRY VDQHMLPQLK DLVNRYQPSL IFSDGEWDHP SDVWRSTEFL AWLYNESPSR
241 EDVIVDDRWG KDTRGHHGGY YTTEYGNIYQ APEDAFQKRK WEECRGMGAS FGYNRNETID
301 EYKPAGELIH LLIELVARGG NLLLDIGPTA DGRIPVIMQQ RLLEIGDWLK ENGEGIYGSS
361 PWRVNAEGDS VRYTTRDGAV YAHLLKWPGA ELALESPKAG GTVEASLLGW PEPLACKVEN
421 GKIHISMPVI PPDNNTIRHA FVIRLKGVE
```

(51) Int. Cl.
*C12N 9/24* (2006.01)
*C07K 1/13* (2006.01)
*C12P 21/00* (2006.01)

(52) U.S. Cl.
CPC ............... *C12Y 302/01023* (2013.01); *C12Y 302/01111* (2013.01); *C12Y 302/01127* (2013.01)

(56) References Cited

OTHER PUBLICATIONS

Cohen, et al., Anal Biochem, 211(2):279-287, 1993.
Lauber, et al., Annal Chem, 87, 5401-5409, 2015.
Stockmann, et al., Anal Chem, 87:8316-8322, 2015.
Furste, et al., Gene, 48:119-131, 1986.
Wong-Madden, et al., Glycobiology, 5:19-28, 1995.
O'Flaherty, et al., J Proteome Res. 16:4237-4234, 2017.
Vainauskas, Scientific Reports, 2018 8: 9504.
Cohen, et al, Anal Biochem, 211(2):279-87, 1993.
Ferrara.,et al. Biotechnol. Bioeng., 93, 851-861, 2006.
Ferrara, et al. Proc. Natl. Acad. Sci. U. S. A, 108, 12669-12674, 2011.
Collin, et al. EMBO J., 20, 3046-3055, 2001.
Li, et al. J. Biol. Chem., 291, 16508-16518, 2016.
Tsai, et al. ACS Chem. Biol.,12, 63-72, 2017.
Speth et al., Gen Bank KXK31601.1, Feb. 24, 2016.

* cited by examiner

Alpha-L-fucosidase of Omnitrophica bacterium OLB16 (SEQ ID NO: 1):

```
  1  MRYILAVLLM VGMMAGAAATA VTYEPTWESL DSRPNPAWFD EAKFGIFIHW GVYAVPAWGS
 61  KGKYSEWYWN DMMDPNGETW KFHLKTYGED FKYQDFAPMF KAEMFDPAQW ADIFARSGAK
121  YVVLTSKHHE GFCLWPSPDS WNWNSVDIGP HRDLCGDLTQ AVRDRGLKMG FYYSLYEWFN
181  PIYKTDVHRY VDQHMLPQLK DLVNRYQPSL IFSDGEWDHP SDVWRSTEFL AWLYNESPSR
241  EDVIVDDRWG KDTRGHHGGY YTTEYGNIYQ APEDAFQKRK WEECRGMGAS FGYNRNETID
301  EYKPAGELIH LLIELVARGG NLLLDIGPTA DGRIPVIMQQ RLLEIGDWLK ENGEGIYGSS
361  PWRVNAEGDS VRYTTRDGAV YAHLLKWPGA ELALESPKAG GTVEASLLGW PEPLACKVEN
421  GKIHISMPVI PPDNNTIRHA FVIRLKGVE
```

FIG. 14B(iii)

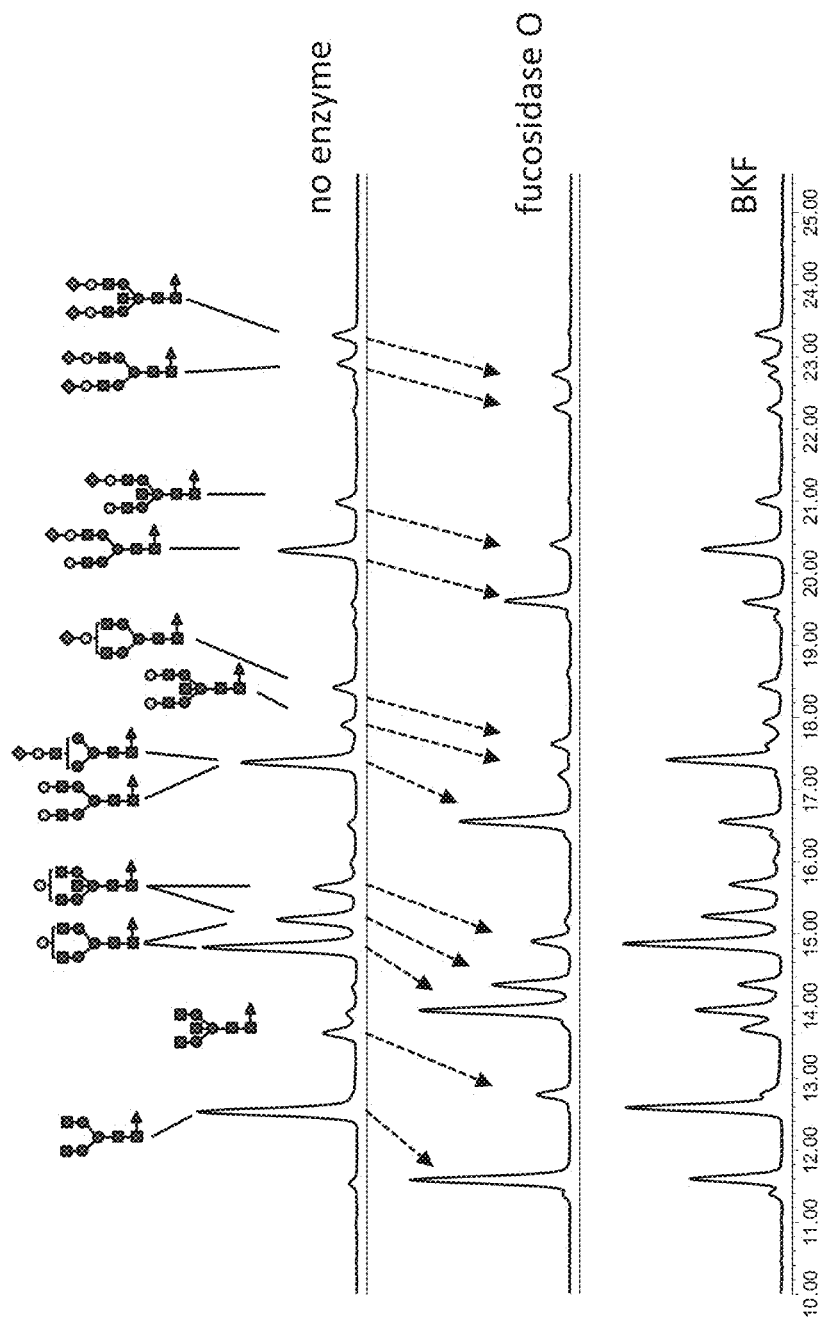

```
                        SEQUENCE LISTING

<160> NUMBER OF SEQ ID NOS: 12

<210> SEQ ID NO 1
<211> LENGTH: 449
<212> TYPE: PRT
<213> ORGANISM: Artificial Sequence
<220> FEATURE:
<223> OTHER INFORMATION: Syntetic construct

<400> SEQUENCE: 1

Met Arg Tyr Ile Leu Ala Val Leu Leu Met Val Gly Met Met Ala Gly
1               5                   10                  15

Ala Ala Thr Ala Val Thr Tyr Glu Pro Thr Trp Glu Ser Leu Asp Ser
                20                  25                  30

Arg Pro Asn Pro Ala Trp Phe Asp Glu Ala Lys Phe Gly Ile Phe Ile
            35                  40                  45

His Trp Gly Val Tyr Ala Val Pro Ala Trp Gly Ser Lys Gly Lys Tyr
        50                  55                  60

Ser Glu Trp Tyr Trp Asn Asp Met Met Asp Pro Asn Gly Glu Thr Trp
65                  70                  75                  80

Lys Phe His Leu Lys Thr Tyr Gly Glu Asp Lys Phe Tyr Gln Asp Phe
                85                  90                  95

Ala Pro Met Phe Lys Ala Glu Met Phe Asp Pro Ala Gln Trp Ala Asp
                100                 105                 110

Ile Phe Ala Arg Ser Gly Ala Lys Tyr Val Val Leu Thr Ser Lys His
            115                 120                 125

His Glu Gly Phe Cys Leu Trp Pro Ser Pro Asp Ser Trp Asn Trp Asn
        130                 135                 140

Ser Val Asp Ile Gly Pro His Arg Asp Leu Cys Gly Asp Leu Thr Gln
145                 150                 155                 160

Ala Val Arg Asp Arg Gly Leu Lys Met Gly Phe Tyr Tyr Ser Leu Tyr
                165                 170                 175

Glu Trp Phe Asn Pro Ile Tyr Lys Thr Asp Val His Arg Tyr Val Asp
            180                 185                 190

Gln His Met Leu Pro Gln Leu Lys Asp Leu Val Asn Arg Tyr Gln Pro
        195                 200                 205
```

```
Ser Leu Ile Phe Ser Asp Gly Glu Trp Asp His Pro Ser Asp Val Trp
    210                 215                 220
Arg Ser Thr Glu Phe Leu Ala Trp Leu Tyr Asn Glu Ser Pro Ser Arg
225                 230                 235                 240
Glu Asp Val Ile Val Asp Asp Arg Trp Gly Lys Asp Thr Arg Gly His
                245                 250                 255
His Gly Gly Tyr Tyr Thr Thr Glu Tyr Gly Asn Ile Tyr Gln Ala Pro
            260                 265                 270
Glu Asp Ala Phe Gln Lys Arg Lys Trp Glu Glu Cys Arg Gly Met Gly
                275                 280                 285
Ala Ser Phe Gly Tyr Asn Arg Asn Glu Thr Ile Asp Glu Tyr Lys Pro
290                 295                 300
Ala Gly Glu Leu Ile His Leu Leu Ile Glu Leu Val Ala Arg Gly Gly
305                 310                 315                 320
Asn Leu Leu Leu Asp Ile Gly Pro Thr Ala Asp Gly Arg Ile Pro Val
                325                 330                 335
Ile Met Gln Gln Arg Leu Leu Gly Ile Gly Asp Trp Leu Lys Glu Asn
                340                 345                 350
Gly Glu Gly Ile Tyr Gly Ser Ser Pro Trp Arg Val Asn Ala Glu Gly
            355                 360                 365
Asp Ser Val Arg Tyr Thr Thr Arg Asp Gly Ala Val Tyr Ala His Leu
370                 375                 380
Leu Lys Trp Pro Gly Ala Glu Leu Ala Leu Glu Ser Pro Lys Ala Gly
385                 390                 395                 400
Gly Thr Val Glu Ala Ser Leu Leu Gly Trp Pro Glu Pro Leu Ala Cys
                405                 410                 415
Lys Val Glu Asn Gly Lys Ile His Ile Ser Met Pro Val Ile Pro Pro
                420                 425                 430
Asp Asn Asn Thr Ile Arg His Ala Phe Val Ile Arg Leu Lys Gly Val
                435                 440                 445
Glu

<210> SEQ ID NO 2
<211> LENGTH: 283
<212> TYPE: PRT
<213> ORGANISM: Homo sapiens

<400> SEQUENCE: 2

Met Arg Ala Pro Gly Met Arg Ser Arg Pro Ala Gly Pro Ala Leu Leu
1               5                   10                  15
Leu Leu Leu Leu Phe Leu Gly Ala Ala Glu Ser Val Arg Arg Ala Gln
                20                  25                  30
Pro Pro Arg Arg Tyr Thr Pro Asp Trp Pro Ser Leu Asp Ser Arg Pro
                35                  40                  45
Leu Pro Ala Trp Phe Asp Glu Ala Lys Phe Gly Val Phe Ile His Trp
            50                  55                  60
Gly Val Phe Ser Val Pro Ala Trp Gly Ser Glu Trp Phe Trp Trp His
65              70                  75                  80
Trp Gln Gly Glu Gly Arg Pro Gln Tyr Gln Arg Phe Met Arg Asp Asn
                85                  90                  95
Tyr Pro Pro Gly Phe Ser Tyr Ala Asp Phe Gly Pro Gln Phe Thr Ala
            100                 105                 110
Arg Phe Phe His Pro Glu Glu Trp Ala Asp Leu Phe Gln Ala Ala Gly
            115                 120                 125
```

```
Ala Lys Tyr Val Val Leu Thr Thr Lys His His Glu Gly Phe Thr Asn
    130                 135                 140
Trp Pro Ser Pro Val Ser Trp Asn Trp Asn Ser Lys Asp Val Gly Pro
145                 150                 155                 160
His Arg Asp Leu Val Gly Glu Leu Gly Thr Ala Leu Arg Lys Arg Asn
                165                 170                 175
Ile Arg Tyr Gly Leu Tyr His Ser Leu Leu Glu Trp Phe His Pro Leu
            180                 185                 190
Tyr Leu Leu Asp Lys Lys Asn Gly Phe Lys Thr Gln His Phe Val Ser
        195                 200                 205
Ala Lys Thr Met Pro Glu Leu Tyr Asp Leu Val Asn Ser Tyr Lys Pro
    210                 215                 220
Asp Leu Ile Trp Ser Asp Gly Glu Trp Glu Cys Pro Asp Thr Tyr Trp
225                 230                 235                 240
Asn Ser Thr Asn Phe Leu Ser Trp Leu Tyr Asn Asp Ser Pro Val Lys
                245                 250                 255
Asp Glu Val Val Val Asn Asp Arg Trp Gly Gln Asn Cys Ser Cys His
            260                 265                 270
His Gly Gly Tyr Tyr Asn Cys Glu Asp Lys Phe
        275                 280
```

<210> SEQ ID NO 3
<211> LENGTH: 285
<212> TYPE: PRT
<213> ORGANISM: Macaca fascicularis

<400> SEQUENCE: 3

```
Met Arg Ala Pro Gly Glu Arg Trp Arg Pro Ala Gly Ala Ala Leu Trp
1               5                   10                  15
Leu Leu Leu Leu Leu Leu Leu Leu Gly Ala Thr Glu Ser Val Arg Arg
            20                  25                  30
Ala Gln Pro Leu Arg Arg Tyr Thr Pro Asp Trp Pro Ser Leu Asp Ser
        35                  40                  45
Arg Pro Leu Pro Ser Trp Phe Asp Glu Ala Lys Phe Gly Val Phe Ile
    50                  55                  60
His Trp Gly Val Phe Ser Val Pro Ala Trp Gly Ser Glu Trp Phe Trp
65                  70                  75                  80
Trp Asn Trp Gln Gly Glu Gly Arg Pro Gln Tyr Gln Arg Phe Met Arg
                85                  90                  95
Asp Asn Tyr Pro Pro Gly Ser Ser Tyr Ala Asp Phe Gly Pro Gln Phe
            100                 105                 110
Thr Ala Arg Phe Phe His Pro Glu Glu Trp Ala Asp Leu Phe Gln Ala
        115                 120                 125
Ala Gly Ala Lys Tyr Val Val Leu Thr Thr Lys His His Glu Gly Phe
    130                 135                 140
Thr Asn Trp Pro Ser Pro Val Ser Trp Asn Trp Asn Ser Lys Asp Val
145                 150                 155                 160
Gly Pro His Arg Asp Leu Val Gly Glu Leu Gly Thr Ala Leu Arg Lys
                165                 170                 175
Arg Asn Ile Arg Tyr Gly Leu Tyr His Ser Leu Leu Glu Trp Phe His
            180                 185                 190
Pro Leu Tyr Leu Leu Asp Lys Lys Asn Gly Phe Lys Thr Gln Tyr Phe
        195                 200                 205
Val Gly Ala Lys Thr Met Pro Glu Leu Tyr Asp Leu Val Asn Ser Tyr
    210                 215                 220
```

```
Lys Pro Asp Leu Ile Trp Ser Asp Gly Glu Trp Glu Cys Pro Asp Thr
225                 230                 235                 240

Tyr Trp Asn Ser Thr Asn Phe Leu Ser Trp Leu Tyr Asn Asp Ser Pro
            245                 250                 255

Val Lys Asp Glu Val Val Asn Asp Arg Trp Gly Gln Asn Cys Ser
        260                 265                 270

Cys His His Gly Gly Tyr Tyr Asn Cys Glu Asp Lys Phe
        275                 280                 285

<210> SEQ ID NO 4
<211> LENGTH: 286
<212> TYPE: PRT
<213> ORGANISM: Bos taurus

<400> SEQUENCE: 4

Met Arg Ser Trp Val Val Gly Ala Arg Leu Leu Leu Leu Gln Leu
1               5                   10                  15

Val Leu Val Leu Gly Ala Val Arg Leu Pro Pro Cys Thr Asp Pro Arg
            20                  25                  30

His Cys Thr Asp Pro Pro Arg Tyr Thr Pro Asp Trp Pro Ser Leu Asp
            35                  40                  45

Ser Arg Pro Leu Pro Ala Trp Phe Asp Glu Ala Lys Phe Gly Val Phe
    50                  55                  60

Val His Trp Gly Val Phe Ser Val Pro Ala Trp Gly Ser Glu Trp Phe
65                  70                  75                  80

Trp Trp His Trp Gln Gly Glu Lys Leu Pro Gln Tyr Glu Ser Phe Met
                85                  90                  95

Lys Glu Asn Tyr Pro Pro Asp Phe Ser Tyr Ala Asp Phe Gly Pro Arg
            100                 105                 110

Phe Thr Ala Arg Phe Phe Asn Pro Asp Ser Trp Ala Asp Leu Phe Lys
        115                 120                 125

Ala Ala Gly Ala Lys Tyr Val Val Leu Thr Thr Lys His His Glu Gly
    130                 135                 140

Tyr Thr Asn Trp Pro Ser Pro Val Ser Trp Asn Trp Asn Ser Lys Asp
145                 150                 155                 160

Val Gly Pro His Arg Asp Leu Val Gly Glu Leu Gly Thr Ala Ile Arg
                165                 170                 175

Lys Arg Asn Ile Arg Tyr Gly Leu Tyr His Ser Leu Leu Glu Trp Phe
            180                 185                 190

His Pro Leu Tyr Leu Arg Asp Lys Lys Asn Gly Phe Lys Thr Gln Tyr
        195                 200                 205

Phe Val Asn Ala Lys Thr Met Pro Glu Leu Tyr Asp Leu Val Asn Arg
    210                 215                 220

Tyr Lys Pro Asp Leu Ile Trp Ser Asp Gly Glu Trp Glu Cys Pro Asp
225                 230                 235                 240

Thr Tyr Trp Asn Ser Thr Asp Phe Leu Ala Trp Leu Tyr Asn Asp Ser
                245                 250                 255

Pro Val Lys Asp Glu Val Val Asn Asp Arg Trp Gly Gln Asn Cys
        260                 265                 270

Ser Cys His His Gly Gly Tyr Tyr Asn Cys Lys Asp Lys Phe
        275                 280                 285

<210> SEQ ID NO 5
<211> LENGTH: 283
<212> TYPE: PRT
<213> ORGANISM: Canis familiaris
```

<400> SEQUENCE: 5

```
Met Lys Pro Trp Ala Val Gly Leu Gly Pro Pro Pro Ala Val Pro
1               5                   10                  15

Leu Leu Leu Leu Leu Leu Leu Gly Ala Ala Leu Val Arg Ala Ala
                20                  25                  30

Pro Pro Arg Arg Tyr Thr Pro Asp Trp Gln Ser Leu Asp Ser Arg Pro
        35                  40                  45

Leu Pro Asp Trp Phe Asp Lys Ala Lys Phe Gly Val Phe Val His Trp
    50                  55                  60

Gly Glu Phe Ala Val Pro Ala Trp Gly Ser Glu Trp Phe Trp Trp His
65              70                  75                  80

Trp Lys Gly Glu Gly Leu Pro Gln Tyr Glu Gln Phe Met Ser Glu Asn
                85                  90                  95

Tyr Pro Pro Gly Phe Ser Tyr Ala Asp Phe Gly Pro Gln Phe Thr Ala
                100                 105                 110

Arg Phe Phe His Pro Asp Thr Trp Ala Asp Leu Phe Gln Ala Ala Gly
            115                 120                 125

Ala Arg Tyr Val Val Leu Thr Thr Lys His His Glu Gly Phe Thr Asn
130                 135                 140

Trp Pro Ser Ser Val Ser Trp Asn Trp Asn Ser Asn Asp Val Gly Pro
145                 150                 155                 160

His Arg Asp Leu Val Gly Glu Leu Gly Arg Ala Leu Arg Lys Arg Asn
                165                 170                 175

Ile Arg Tyr Gly Leu Tyr His Ser Leu Leu Glu Trp Phe His Pro Leu
                180                 185                 190

Tyr Leu Leu Asp Lys Lys Asn Asn Phe Lys Thr Gln Phe Phe Val Arg
            195                 200                 205

Ala Lys Thr Met Pro Glu Leu Tyr Asp Leu Val Asn Arg Tyr Glu Pro
210                 215                 220

Asp Leu Ile Trp Ser Asp Gly Glu Trp Lys Cys Pro Asp Thr Tyr Trp
225                 230                 235                 240

Asn Ser Thr Glu Phe Leu Ser Trp Leu Tyr Asn Asp Ser Pro Val Lys
                245                 250                 255

Asp His Val Val Val Asn Asp Arg Trp Gly Gln Asn Cys Ser Cys His
                260                 265                 270

His Gly Gly Tyr Tyr Asn Cys Gln Asp Lys Tyr
            275                 280
```

<210> SEQ ID NO 6
<211> LENGTH: 279
<212> TYPE: PRT
<213> ORGANISM: Rattus norvegicus

<400> SEQUENCE: 6

```
Met Trp Asp Leu Lys Ser Glu Trp Trp Ala Val Gly Phe Gly Leu Leu
1               5                   10                  15

Leu Leu Leu Ala Ala Ser Ala Gln Ala Gly Gly Leu Ala Pro His His
                20                  25                  30

Tyr Thr Pro Asp Trp Pro Ser Leu Asp Ser Arg Pro Leu Pro Arg Trp
            35                  40                  45

Phe Asp Glu Ala Lys Phe Gly Leu Phe Val His Trp Gly Val Tyr Ser
    50                  55                  60

Val Pro Ala Trp Gly Ser Glu Trp Phe Trp Trp His Trp Gln Gly Glu
65              70                  75                  80
```

Gln Ser Ser Ala Tyr Val Arg Phe Met Lys Glu Asn Tyr Pro Pro Gly
                    85                  90                  95

Phe Ser Tyr Ala Asp Phe Ala Pro Gln Phe Thr Ala Arg Phe Phe His
            100                 105                 110

Pro Glu Glu Trp Ala Asp Leu Phe Gln Ala Ala Gly Ala Lys Tyr Val
        115                 120                 125

Val Leu Thr Ala Lys His His Glu Gly Phe Thr Asn Trp Pro Ser Ala
130                 135                 140

Val Ser Trp Asn Trp Asn Ser Lys Asp Val Gly Pro His Arg Asp Leu
145                 150                 155                 160

Val Gly Glu Leu Gly Ala Ala Val Arg Lys Arg Asn Ile Arg Tyr Gly
                165                 170                 175

Leu Tyr His Ser Leu Phe Glu Trp Phe His Pro Leu Tyr Leu Leu Asp
            180                 185                 190

Lys Lys Asn Gly Leu Lys Thr Gln His Phe Val Ser Thr Lys Thr Met
        195                 200                 205

Pro Glu Leu Tyr Asp Leu Val Asn Arg Tyr Lys Pro Asp Leu Ile Trp
    210                 215                 220

Ser Asp Gly Glu Trp Glu Cys Pro Asp Ser Tyr Trp Asn Ser Thr Glu
225                 230                 235                 240

Phe Leu Ala Trp Leu Tyr Asn Glu Ser Pro Val Lys Asp Gln Val Val
                245                 250                 255

Val Asn Asp Arg Trp Gly Gln Asn Cys Ser Cys Arg His Gly Gly Tyr
            260                 265                 270

Tyr Asn Cys Glu Asp Lys Tyr
        275

<210> SEQ ID NO 7
<211> LENGTH: 269
<212> TYPE: PRT
<213> ORGANISM: Mus musculus

<400> SEQUENCE: 7

Met Leu Leu Leu Leu Leu Leu Leu Val Ala Ala Gln Ala Val
1               5                   10                  15

Ala Leu Ala Pro Arg Arg Phe Thr Pro Asp Trp Gln Ser Leu Asp Ser
                20                  25                  30

Arg Pro Leu Pro Ser Trp Phe Asp Glu Ala Lys Phe Gly Val Phe Val
            35                  40                  45

His Trp Gly Val Phe Ser Val Pro Ala Trp Gly Ser Glu Trp Phe Trp
        50                  55                  60

Trp His Trp Gln Gly Asp Arg Met Pro Ala Tyr Gln Arg Phe Met Thr
65                  70                  75                  80

Glu Asn Tyr Pro Pro Gly Phe Ser Tyr Ala Asp Phe Ala Pro Gln Phe
                85                  90                  95

Thr Ala Arg Phe Phe His Pro Asp Gln Trp Ala Glu Leu Phe Gln Ala
            100                 105                 110

Ala Gly Ala Lys Tyr Val Val Leu Thr Thr Lys His His Glu Gly Phe
        115                 120                 125

Thr Asn Trp Pro Ser Pro Val Ser Trp Asn Trp Asn Ser Lys Asp Val
    130                 135                 140

Gly Pro His Arg Asp Leu Val Gly Glu Leu Gly Ala Ala Val Arg Lys
145                 150                 155                 160

Arg Asn Ile Arg Tyr Gly Leu Tyr His Ser Leu Leu Glu Trp Phe His
                165                 170                 175

```
Pro Leu Tyr Leu Leu Asp Lys Lys Asn Gly Phe Lys Thr Gln His Phe
            180                 185                 190

Val Arg Ala Lys Thr Met Pro Glu Leu Tyr Asp Leu Val Asn Ser Tyr
        195                 200                 205

Lys Pro Asp Leu Ile Trp Ser Asp Gly Glu Trp Glu Cys Pro Asp Thr
    210                 215                 220

Tyr Trp Asn Ser Thr Ser Phe Leu Ala Trp Leu Tyr Asn Asp Ser Pro
225                 230                 235                 240

Val Lys Asp Glu Val Ile Val Asn Asp Arg Trp Gly Gln Asn Cys Ser
                245                 250                 255

Cys His His Gly Gly Tyr Tyr Asn Cys Gln Asp Lys Tyr
            260                 265

<210> SEQ ID NO 8
<211> LENGTH: 279
<212> TYPE: PRT
<213> ORGANISM: Pongo pygmaeus

<400> SEQUENCE: 8

Met Arg Pro Gln Glu Leu Pro Arg Leu Ala Phe Pro Leu Leu Leu Leu
1               5                   10                  15

Leu Leu Leu Pro Pro Pro Cys Pro Ala His Ser Ala Thr Arg Phe
                20                  25                  30

Asp Pro Thr Trp Glu Ser Leu Asp Ala Arg Gln Leu Pro Ala Trp Phe
            35                  40                  45

Asp Gln Ala Lys Phe Gly Ile Phe Ile His Trp Gly Val Phe Ser Val
        50                  55                  60

Pro Ser Phe Gly Ser Glu Trp Phe Trp Trp Tyr Trp Gln Lys Glu Lys
65                  70                  75                  80

Ile Pro Lys Tyr Val Glu Phe Met Lys Asp Asn Tyr Pro Pro Ser Phe
                85                  90                  95

Lys Tyr Glu Asp Phe Gly Pro Leu Phe Thr Ala Lys Phe Phe Asn Ala
            100                 105                 110

Asn Gln Trp Ala Asp Ile Phe Gln Ala Ser Gly Ala Lys Tyr Ile Val
        115                 120                 125

Leu Thr Ser Lys His His Lys Gly Phe Thr Leu Trp Gly Ser Glu Tyr
130                 135                 140

Ser Trp Asn Trp Asn Ala Ile Asp Glu Gly Pro Lys Arg Asp Ile Val
145                 150                 155                 160

Lys Glu Leu Glu Val Ala Ile Arg Asn Arg Thr Asp Leu Arg Phe Gly
                165                 170                 175

Leu Tyr Tyr Ser Leu Phe Glu Trp Phe His Pro Leu Phe Leu Glu Asp
            180                 185                 190

Glu Ser Ser Ser Phe His Lys Arg Gln Phe Pro Val Ser Lys Thr Leu
        195                 200                 205

Pro Glu Leu Tyr Glu Leu Val Asn Asn Tyr Gln Pro Glu Val Leu Trp
    210                 215                 220

Ser Asp Gly Asp Gly Gly Ala Pro Asp Gln Tyr Trp Asn Ser Thr Gly
225                 230                 235                 240

Phe Leu Ala Trp Leu Tyr Asn Glu Ser Pro Val Arg Glu Thr Val Val
                245                 250                 255

Thr Asn Asp Arg Trp Gly Ala Gly Ser Ile Tyr Lys His Gly Gly Phe
            260                 265                 270

Tyr Thr Cys Ser Asp Arg Tyr
275
```

-continued

```
<210> SEQ ID NO 9
<211> LENGTH: 281
<212> TYPE: PRT
<213> ORGANISM: Homo sapiens

<400> SEQUENCE: 9

Met Arg Pro Gln Glu Leu Pro Arg Leu Ala Phe Pro Leu Leu Leu
1               5                   10                  15

Leu Leu Leu Leu Leu Pro Pro Pro Cys Pro Ala His Ser Ala Thr
                20                  25                  30

Arg Phe Asp Pro Thr Trp Glu Ser Leu Asp Ala Arg Gln Leu Pro Ala
                35                  40                  45

Trp Phe Asp Gln Ala Lys Phe Gly Ile Phe Ile His Trp Gly Val Phe
    50                  55                  60

Ser Val Pro Ser Phe Gly Ser Glu Trp Phe Trp Trp Tyr Trp Gln Lys
65                  70                  75                  80

Glu Lys Ile Pro Lys Tyr Val Glu Phe Met Lys Asp Asn Tyr Pro Pro
                85                  90                  95

Ser Phe Lys Tyr Glu Asp Phe Gly Pro Leu Phe Thr Ala Lys Phe Phe
                100                 105                 110

Asn Ala Asn Gln Trp Ala Asp Ile Phe Gln Ala Ser Gly Ala Lys Tyr
            115                 120                 125

Ile Val Leu Thr Ser Lys His His Glu Gly Phe Thr Leu Trp Gly Ser
130                 135                 140

Glu Tyr Ser Trp Asn Trp Asn Ala Ile Asp Glu Gly Pro Lys Arg Asp
145                 150                 155                 160

Ile Val Lys Glu Leu Glu Val Ala Ile Arg Asn Arg Thr Asp Leu Arg
                165                 170                 175

Phe Gly Leu Tyr Tyr Ser Leu Phe Glu Trp Phe His Pro Leu Phe Leu
            180                 185                 190

Glu Asp Glu Ser Ser Phe His Lys Arg Gln Phe Pro Val Ser Lys
            195                 200                 205

Thr Leu Pro Glu Leu Tyr Glu Leu Val Asn Asn Tyr Gln Pro Glu Val
210                 215                 220

Leu Trp Ser Asp Gly Asp Gly Gly Ala Pro Asp Gln Tyr Trp Asn Ser
225                 230                 235                 240

Thr Gly Phe Leu Ala Trp Leu Tyr Asn Glu Ser Pro Val Arg Gly Thr
                245                 250                 255

Val Val Thr Asn Asp Arg Trp Gly Ala Gly Ser Ile Cys Lys His Gly
                260                 265                 270

Gly Phe Tyr Thr Cys Ser Asp Arg Tyr
            275                 280

<210> SEQ ID NO 10
<211> LENGTH: 273
<212> TYPE: PRT
<213> ORGANISM: Rattus norvegicus

<400> SEQUENCE: 10

Met Arg Leu Gly Leu Leu Met Phe Leu Pro Leu Leu Leu Ala Thr
1               5                   10                  15

Arg Tyr Arg Ala Val Thr Ala Leu Ser Tyr Asp Pro Thr Trp Glu Ser
                20                  25                  30

Leu Asp Arg Arg Pro Leu Pro Ala Trp Phe Asp Gln Ala Lys Phe Gly
            35                  40                  45
```

```
Ile Phe Ile His Trp Gly Val Phe Ser Val Pro Ser Phe Gly Ser Glu
 50                  55                  60
Trp Phe Trp Trp Tyr Trp Gln Lys Glu Arg Arg Pro Lys Phe Val Asp
 65                  70                  75                  80
Phe Met Asp Asn Asn Tyr Pro Pro Gly Phe Lys Tyr Glu Asp Phe Gly
                 85                  90                  95
Val Leu Phe Thr Ala Lys Tyr Phe Asn Ala Asn Gln Trp Ala Asp Leu
                100                 105                 110
Leu Gln Ala Ser Gly Ala Lys Tyr Val Val Leu Thr Ser Lys His His
                115                 120                 125
Glu Gly Phe Thr Leu Trp Gly Ser Ala His Ser Trp Asn Trp Asn Ala
            130                 135                 140
Val Asp Glu Gly Pro Lys Arg Asp Ile Val Lys Glu Leu Glu Val Ala
145                 150                 155                 160
Val Arg Asn Arg Thr Asp Leu His Phe Gly Leu Tyr Tyr Ser Leu Phe
                165                 170                 175
Glu Trp Phe His Pro Leu Phe Leu Glu Asp Gln Ser Ser Ala Phe Gln
            180                 185                 190
Lys Gln Arg Phe Pro Val Ala Lys Thr Leu Pro Glu Leu Tyr Glu Leu
        195                 200                 205
Val Thr Lys Tyr Gln Pro Glu Val Leu Trp Ser Asp Gly Asp Gly Gly
210                 215                 220
Ala Pro Asp His Tyr Trp Asn Ser Thr Asp Phe Leu Ala Trp Leu Tyr
225                 230                 235                 240
Asn Glu Ser Pro Val Arg Asp Thr Val Val Thr Asn Asp Arg Trp Gly
                245                 250                 255
Ala Gly Ser Ile Cys Lys His Gly Gly Tyr Tyr Thr Cys Ser Asp Arg
            260                 265                 270
Tyr

<210> SEQ ID NO 11
<211> LENGTH: 275
<212> TYPE: PRT
<213> ORGANISM: Mus musculus

<400> SEQUENCE: 11

Met Arg Leu Gly Phe Leu Met Leu Leu Pro Leu Leu Leu Pro Leu
1                5                  10                  15
Leu Arg Pro Trp Gly Val Thr Arg Ala Leu Ser Tyr Asp Pro Thr Trp
                20                  25                  30
Glu Ser Leu Asp Arg Arg Pro Leu Pro Ala Trp Phe Asp Gln Ala Lys
            35                  40                  45
Phe Gly Ile Phe Ile His Trp Gly Val Phe Ser Val Pro Ser Phe Gly
        50                  55                  60
Ser Glu Trp Phe Trp Trp Tyr Trp Gln Lys Glu Lys Pro Gln Phe
65                  70                  75                  80
Val Asp Phe Met Asn Asn Tyr Ala Pro Gly Phe Lys Tyr Glu Asp
                85                  90                  95
Phe Val Val Leu Phe Thr Ala Lys Tyr Phe Asn Ala Asn Gln Trp Ala
                100                 105                 110
Asp Ile Leu Gln Ala Ser Gly Ala Lys Tyr Val Val Phe Thr Ser Lys
            115                 120                 125
His His Glu Gly Phe Thr Met Trp Gly Ser Asp Arg Ser Trp Asn Trp
        130                 135                 140
```

Asn Ala Val Asp Glu Gly Pro Lys Arg Asp Ile Val Lys Glu Leu Glu
145                 150                 155                 160

Val Ala Val Arg Asn Arg Thr Gly Leu His Phe Gly Leu Tyr Tyr Ser
            165                 170                 175

Leu Phe Glu Trp Phe His Pro Leu Phe Leu Glu Asp Gln Ser Ser Ser
            180                 185                 190

Phe Gln Lys Gln Arg Phe Pro Val Ser Lys Thr Leu Pro Glu Leu Tyr
            195                 200                 205

Glu Leu Val Asn Arg Tyr Gln Pro Glu Val Leu Trp Ser Asp Gly Asp
            210                 215                 220

Gly Gly Ala Pro Asp His Tyr Trp Asn Ser Thr Gly Phe Leu Ala Trp
225                 230                 235                 240

Leu Tyr Asn Glu Ser Pro Val Arg Lys Thr Val Thr Asn Asp Arg
            245                 250                 255

Trp Gly Val Gly Ser Ile Cys Lys His Gly Gly Tyr Tyr Thr Cys Ser
            260                 265                 270

Asp Arg Tyr
        275

<210> SEQ ID NO 12
<211> LENGTH: 269
<212> TYPE: PRT
<213> ORGANISM: Unknown
<220> FEATURE:
<223> OTHER INFORMATION: Omnitrophica

<400> SEQUENCE: 12

Met Arg Tyr Ile Leu Ala Val Leu Leu Met Val Gly Met Met Ala Gly
1               5                   10                  15

Ala Ala Thr Ala Val Thr Tyr Glu Pro Thr Trp Glu Ser Leu Asp Ser
            20                  25                  30

Arg Pro Asn Pro Ala Trp Phe Asp Glu Ala Lys Phe Gly Ile Phe Ile
            35                  40                  45

His Trp Gly Val Tyr Ala Val Pro Ala Trp Gly Ser Lys Gly Lys Tyr
    50                  55                  60

Ser Glu Trp Tyr Trp Asn Asp Met Met Asp Pro Asn Gly Glu Thr Trp
65                  70                  75                  80

Lys Phe His Leu Lys Thr Tyr Gly Glu Asp Phe Lys Tyr Gln Asp Phe
                85                  90                  95

Ala Pro Met Phe Lys Ala Glu Met Phe Asp Pro Ala Gln Trp Ala Asp
            100                 105                 110

Ile Phe Ala Arg Ser Gly Ala Lys Tyr Val Val Leu Thr Ser Lys His
            115                 120                 125

His Glu Gly Phe Cys Leu Trp Pro Ser Pro Asp Ser Trp Asn Trp Asn
            130                 135                 140

Ser Val Asp Ile Gly Pro His Arg Asp Leu Cys Gly Asp Leu Thr Gln
145                 150                 155                 160

Ala Val Arg Asp Arg Gly Leu Lys Met Gly Phe Tyr Tyr Ser Leu Tyr
            165                 170                 175

Glu Trp Phe Asn Pro Ile Tyr Lys Thr Asp Val His Arg Tyr Val Asp
            180                 185                 190

Gln His Met Leu Pro Gln Leu Lys Asp Leu Val Asn Arg Tyr Gln Pro
            195                 200                 205

Ser Leu Ile Phe Ser Asp Gly Glu Trp Asp His Pro Ser Asp Val Trp
210                 215                 220

```
Arg Ser Thr Glu Phe Leu Ala Trp Leu Tyr Asn Glu Ser Pro Ser Arg
225                 230                 235                 240

Glu Asp Val Ile Val Asp Asp Arg Trp Gly Lys Asp Thr Arg Gly His
                245                 250                 255

His Gly Gly Tyr Tyr Thr Thr Glu Tyr Gly Asn Ile Tyr
            260             265
```

CLEAVAGE OF FUCOSE IN N-GLYCANS

CROSS REFERENCE

This application claims the benefit of U.S. Provisional Application No. 62/472,994, filed Mar. 17, 2017 and U.S. Provisional Application No. 62/474,860, filed Mar. 22, 2017 herein incorporated by reference.

BACKGROUND

The terms glycan and polysaccharide are defined by IUPAC as synonyms meaning "compounds consisting of a large number of monosaccharides linked glycosidically." However, in practice the term glycan may also be used to refer to the carbohydrate portion of a glycoconjugate, such as a glycoprotein, glycolipid, or a proteoglycan, even if the carbohydrate is only an oligosaccharide.

Many secreted eukaryotic proteins possess post-translational carbohydrate modifications of certain asparagine residues (N-glycans). N-glycans become attached to proteins in the endoplasmic reticulum of eukaryotic cells on the nitrogen (N) in the side chain of asparagine in the sequon of a protein. The sequon is an Asn-X-Ser or Asn-X-Thr sequence, where X is any amino acid except proline. N-Glycans are commonly comprised of the sugars galactose, N-acetylneuraminic acid, N-acetylglucosamine (GlcNAc), fucose, and mannose but may also contain other sugars such as N-acetylgalactosamine and N-glycolylneuraminic acid.

Many classes of biologic drugs (e.g., antibodies, fusion proteins, growth factors, cytokines, etc.) are glycoproteins that possess N-glycans. The composition of these glycans can affect the stability, bioactivity, and serum half-life of a biologic drug. As such, glycan structure is designated a critical quality attribute (CQA) that must be monitored during biologic manufacturing, and the glycan profile of a finished product is used to assess the consistency of a manufacturing process from batch to batch.

To assess their composition, glycans can be structurally profiled using a variety of analytical methods including liquid chromatography, mass spectrometry, or capillary electrophoresis. Additionally, enzymes that remove sugars from the non-reducing end of glycans (exoglycosidases) can be used in concert with these analytical methods to sequence glycans and provide an orthogonal assessment of a glycan's structure.

The past decade has seen many advances in the structural analysis of N-glycans. In general, analytical workflows have significantly increased in speed, throughput and sensitivity. This progress has been driven by improvements to nearly every aspect of workflow design including instrument sensitivity, separations technologies, sample preparation and computational analysis of data. Within the past few years, sample preparation for N-glycan profiling has changed dramatically. Improved reagents and methods have simplified and shortened the process of releasing and fluorescently labeling N-glycans. For structural profiling, N-glycans are typically first removed from a peptide or protein using the enzyme PNGase F (New England Biolabs, Ipswich, Mass.). New formats of PNGase F have substantially improved the speed and completeness of N-glycan release from proteins (see for example US 2015/0346194). Following their release, N-glycans are then fluorescently labeled on their reducing end to enable their ultimate detection during downstream analyses. Recently, new chemistries for label attachment have given rise to a new generation of fluorescent labels that offer "instant" labeling of N-glycans and improved sensitivity in downstream analytical methods such as liquid chromatography, mass spectrometry, and capillary electrophoresis (see for example Cohen, et al., Anal Biochem, 211(2):279-287, 1993; US 2012/0107942; and WO 2013/049622).

For decades, exoglycosidases have been used to assist in structural determination of glycans. These enzymes sequentially remove specific terminal sugars from oligosaccharides. Specific and complete removal of the targeted sugar by the exoglycosidase is critical in order to precisely characterize the structure of glycan. Arrays of exoglycosidases with various different specificities can be used to fully identify and order the sugars in N-glycan (and other glycans). The field has typically utilized a series of well-characterized and commercially available exoglycosidases for glycan characterization. These enzymes have performed well in the presence of traditional fluorescent labels that have been attached to N-glycans via Schiff-base chemistry although these reactions can be rather slow. There is, however, a problem with the performance of certain enzymes in the presence of fluorescent labels that have been attached to the glycosylamine at the reducing end of N-glycans via amine reactive chemistry (e.g. reactive carbamate chemistry). For example, one exoglycosidase commonly used in such assays, bovine kidney fucosidase (BKF), does not effectively cleave α(1,6) linked fucose from the core of N-glycans that have been labeled with this class of fluorescent labels. This problem is a major new hurdle for improved methods of enzyme-based structure verification of N-glycans. Another challenge has been performing a defucosylation reaction on a complex N-glycan attached to the glycoprotein or glycopeptide without having to denature the protein or first cleave at least in part, the N-glycan.

SUMMARY

In general, a composition that is a reaction mix is provided that includes (a) an α-L-fucosidase having an amino acid sequence that is at least 90% identical to amino acids 23-359 of sequence of SEQ ID NO:1; and (b) a conjugate comprising an N-glycan and a label.

In one aspect, the label comprises a fluorophore and/or a charge tag. In various aspects of the reaction mix, the N-glycan of the conjugate comprises a core fucose; the N-glycan is linked to the label via the reducing end of the N-glycan; the N-glycan is from a therapeutic glycoprotein and/or the N-glycan is linked to the label via amine reactive chemistry or by a Schiff base condensation reaction and reduction.

In various aspects of the reaction mix, the conjugate is made by reacting an amine at the reducing end of an N-glycan with amine-reactive label; and/or the conjugate is the product of a reaction between an amine functionalized label and an aldehyde group at the reducing end of the N-glycan.

Other aspects of the reaction mix include in addition to the α1-6 fucosidase, one or more exoglycosidases selected from the group consisting of: α2-3 neuraminidase S, α2-3,6,8,9 neuraminidase A, α1-3,4,6 galactosidase, β1-4 galactosidase, β-N-acetylglucosaminidase S, and α1-2,3,6 mannosidase where the enzymes are combined in the same buffer. In another aspect, the reaction mix has a pH in the range of pH 3.0 to pH 5.5.

In general, an enzyme mix is provided that includes preferably in a single buffer (a) an α-fucosidase having an amino acid sequence that is at least 90% identical to amino acids 23-359 of sequence of SEQ ID NO:1; and (b) one or more additional exoglycosidases other than *Omnitrophica* exoglycosidases that do not naturally occur together in a cell and are preferably derived from multiple different cell sources. At least one exoglucosidase is preferably derived from a mammalian source. The exoglycosidase(s) may be selected from the group consisting of: α2-3 neuraminidase S, α2-3,6,8,9 neuraminidase A, α1-3,4,6 galactosidase, β1-4 galactosidase, β-N-acetylglucosaminidase S, and α1-2,3,6 mannosidase. In one aspect, none of the one or more exoglycosidases in the enzyme mix is glycosylated. In one aspect, the enzyme mix includes the one or more exoglycosidases selected from the group consisting of: NAN1, ABS, CBG, SPG, GUH and JBM. In other aspects, the enzyme mix comprises two or more of the exoglycosidases; or three or more of the exoglycosidases. In one aspect, the enzyme mix comprises α2-3 neuraminidase S, α2-3,6,8,9 neuraminidase A, α1-3,4,6 galactosidase, β1-4 galactosidase and β-N-acetylglucosaminidase S.

In general, a kit is provided that includes (a) a α-fucosidase having an amino acid sequence that is at least 90% identical to amino acids 23-269 of sequence of SEQ ID NO:1; and (b) an amine-reactive label or amine functionalized label. In one aspect, the kit further includes PNGase F. In one aspect, the kit includes one or more exoglycosidases selected from the group consisting of: α2-3 neuraminidase S, α2-3,6,8,9 neuraminidase A, α1-3,4,6 galactosidase, β1-4 galactosidase, β-N-acetylglucosaminidase S, and α1-2,3,6 mannosidase. In one aspect, at least one of the one or more exoglycosidases is combined with the α(1,6)-fucosidase in a reaction mixture.

In general, a method is provided for cleaving fucose from an N-glycan, that includes (a) combining: (i) an α-fucosidase having an amino acid sequence that is at least 90% identical to amino acids 23-359 of sequence of SEQ ID NO:1 with (ii) a conjugate comprising an N-glycan and a label to make a reaction mix; and (b) incubating the reaction mix so as to cleave any core α(1,6)-fucose from the N-glycan. In one aspect, step (a) is done at a pH in the range of pH 3.0-pH 5.5. In another aspect, the method further includes: (c) detecting the cleaved glycan or the cleaved fucose after step (b). The detecting may be quantitative. It may be performed by liquid chromatography, mass spectrometry, capillary electrophoresis or any combination thereof. In one aspect, the method further comprises: cleaving an N-glycan from a glycoprotein; and conjugating the reducing end of the N-glycan with an amine-reactive label or an amine functionalized label to produce the conjugate comprising the N-glycan and label. For example, the cleaving may be done using PNGase F. The protein may be a therapeutic glycoprotein.

In general, a method for cleaving fucose from an N-glycan, includes: (a) combining an α-fucosidase having an amino acid sequence that is at least 90% identical to amino acids 23-359 of sequence of SEQ ID NO:1 with an intact N-glycan linked glycoprotein or glycopeptide in a reaction mix; and (b) incubating the reaction mix so as to cleave any core α(1,6)-fucose from the N-glycan. In one aspect the glycoprotein is an antibody.

In general, a reaction mix is provided that includes: (a) an α-L-fucosidase having an amino acid sequence that is at least 90% identical to amino acids 23-359 of sequence of SEQ ID NO:1; and (b) a glycoprotein or glycopeptide comprising an N-glycan that has not been previously modified in vitro. In one aspect, the glycoprotein is an antibody.

BRIEF DESCRIPTION OF THE FIGURES

The patent or application file contains at least one drawing executed in color. Copies of this patent or patent application publication with color drawing(s) will be provided by the Office upon request and payment of the necessary fee.

The skilled artisan will understand that the drawings, described below, are for illustration purposes only. The drawings are not intended to limit the scope of the present teachings in any way FIG. 1 shows the amino acid sequence of the full length α-L-fucosidase from *Omnitrophica* bacterium (449 amino acids). The first 22 amino acids comprise a signal sequence for protein secretion. The underlined portion of the protein (amino acids 23-359) contains the catalytic domain of the enzyme based on sequence alignments with other fucosidases (FIG. 2) and structural analysis (FIG. 3).

Figure 2:
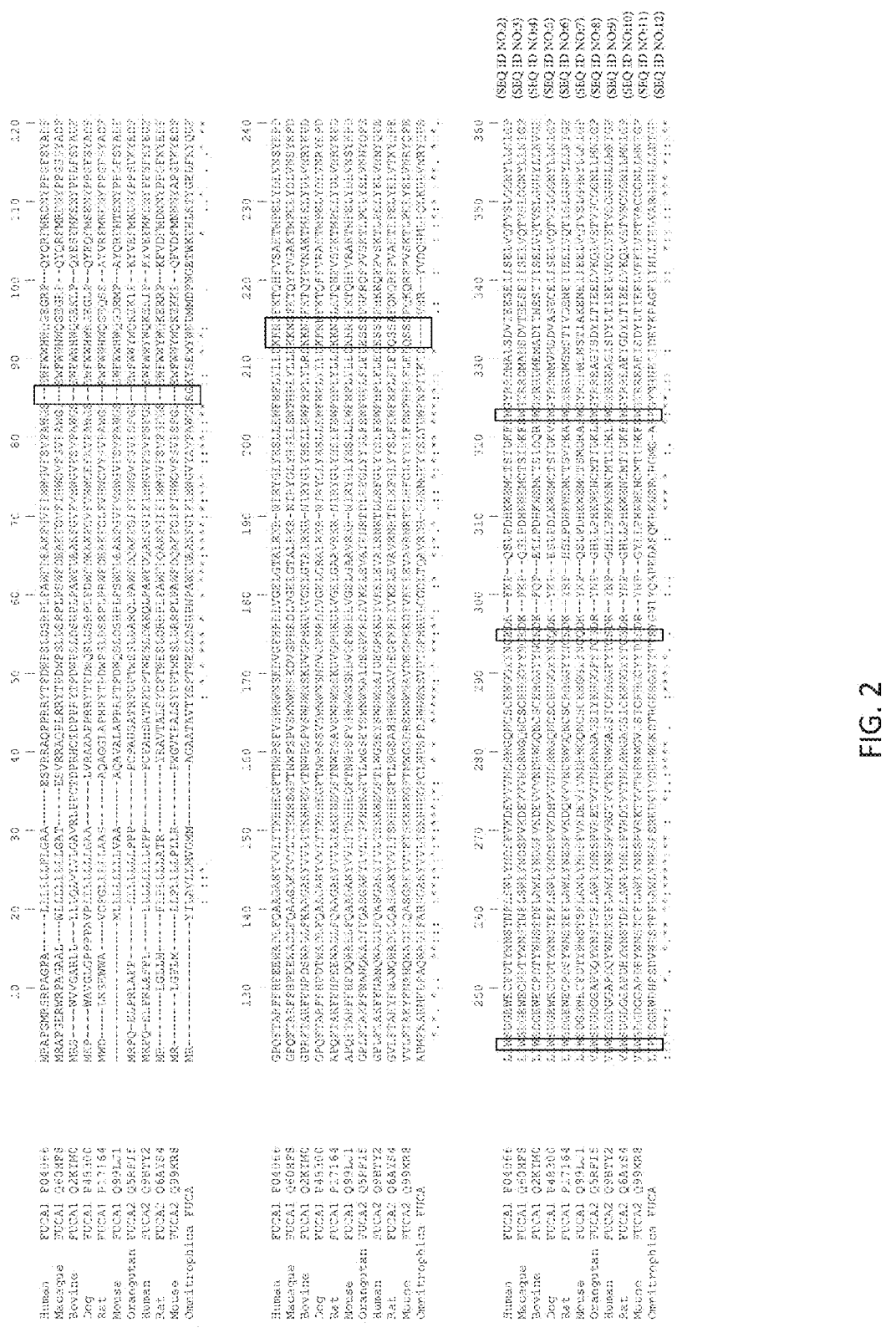

FIG. 2 shows a multiple alignment of the N-terminal part of mammalian FUCA1/2 enzymes (a.k.a. BKF) and *Omnitrophica* α-L-fucosidase. Areas of significant difference between the prokaryotic *Omnitrophica* fucosidase (fucosidase O) (and mammalian fucosidases are identified with boxes. These regions may correlate with each enzyme's different ability to react with labeled N-glycans in which the label is linked to the N-glycan via a glycosylamine linkage or other linkages. From top to bottom: SEQ ID NOs: 2-12, SEQ ID NO: 1.

FIG. 4A shows how a label 2-aminobenzamide (2-AB) can be attached to the reducing end of an N-glycan via a Schiff base condensation reaction. This reaction has many steps, e.g., a hydrolysis reaction and a Schiff base condensation reaction, both of which are slow. As such, labeling N-glycans by Schiff base condensation typically takes longer than an hour.

FIG. 4B shows how a label Instant 2-aminobenzamide ("InstantAB™") can be attached to the reducing end of an N-glycan via activated ester chemistry, where the N-hydroxysuccinimidyl is the leaving group. In this reaction, the amine in the N-glycan in its glycosylamine form attacks the ester carbonyl group to produce a carbamide linkage that links the label and the N-glycan, while the N-hydroxysuccinimidyl leaves.

FIG. 4C shows examples of alternative amine functionalized labels that can be added by Schiff base condensation. Each of these examples contains an amine ($NH_2$) to which a leaving group (e.g., a succinimide group) can be added, thereby producing an amine-reactive label that has an activated group that can undergo a nucleophilic substitution reaction with glycosylamine form of sugars. Examples include procainamide (Proc), aminopyrenetrisulfonic acid (APTS), 2-aminobenzoic acid (2-AA), aminoacridone (AMAC) and 2-aminopyridine (AP).

FIG. 4D provides a generic formula for some activated labels that can be used in the rapid labeling method. In this example, R is fluorescent label that may optionally contain a charge tag (for mass spectrometry analysis). In this example, the activated labels contain an N-hydroxysuccinimidyl carbamate group, although other leaving groups could be used. Examples include 6-aminoquinolyl-N-hydroxysuccinimidylcarbamate (AQC) (fluorescent label) and RapiFluor-MS™ (RFMS) (fluorescent label and charge tag; Waters, Milford, Mass.), the structures for which are shown.

FIG. 4E shows the structures of several alternative amine-reactive labels (i.e., labels that have a reactive group attached to them, where the reactive group can react with an amine to form a covalent bond) that could be used herein.

FIG. 8A shows results for NA2F-InstantAB plus fucosidase.

FIG. 8B shows results for NA2F-Instant Procainamide (InstantPC™) plus fucosidase.

FIG. 8C shows results for N-glycan-RapiFluor-MS plus fucosidase.

Figure 6:
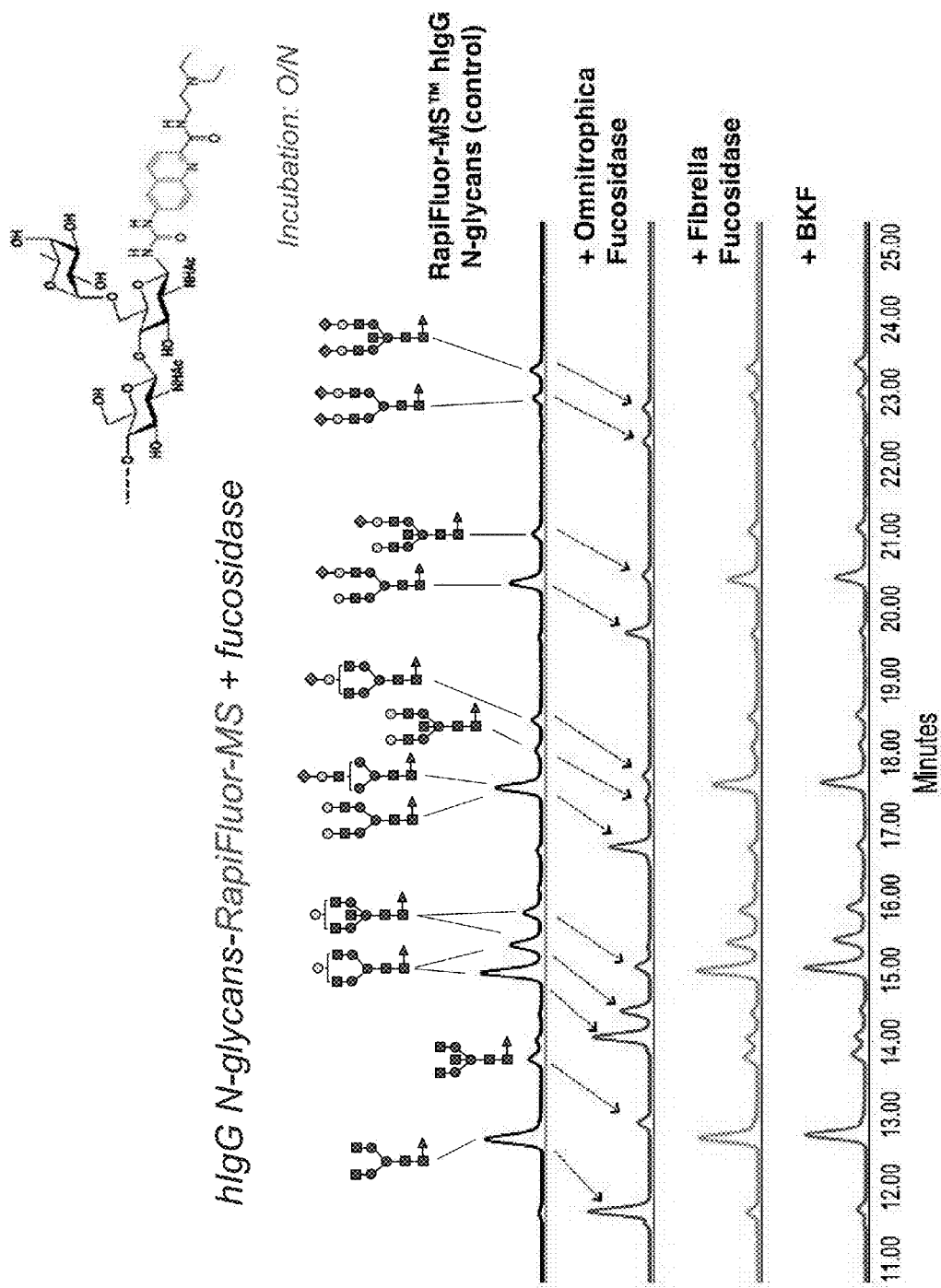
FIG. 6 shows the chromatographic profiles of ultra performance liquid chromatography (UPLC)-separated N-linked glycans of human IgG (hIgG) treated with different fucosidases. The N-glycans are labeled with RapiFluor-MS via a carbamide linkage. The arrows show that *Omnitrophica* fucosidase cleaves α(1,6) fucose from the N-glycans resulting in changes in their migration. Little or no effect was observed with BKF or with *Fibrella* fucosidase over the same time period.

Only *Omnitrophica* fucosidase was able to effect complete cleavage of fucose from every NA2F conjugated to different dyes that contains a carbamide linkage. These results also show that the *Omnitrophica* fucosidase is significantly more active in cleaving α(1,6) fucose than the BKF fucosidase at the comparable concentrations. Note that in FIG. 8C, complete defucosylation of one N-glycan (NGA2F) is highlighted, although the reaction mix contained a plurality of N-glycans released from human IgG (as shown in FIG. 6). The additional peak in the chromatogram (depicted by asterisk) is due to removal of core fucose from a different N-glycan.

Figure 9:
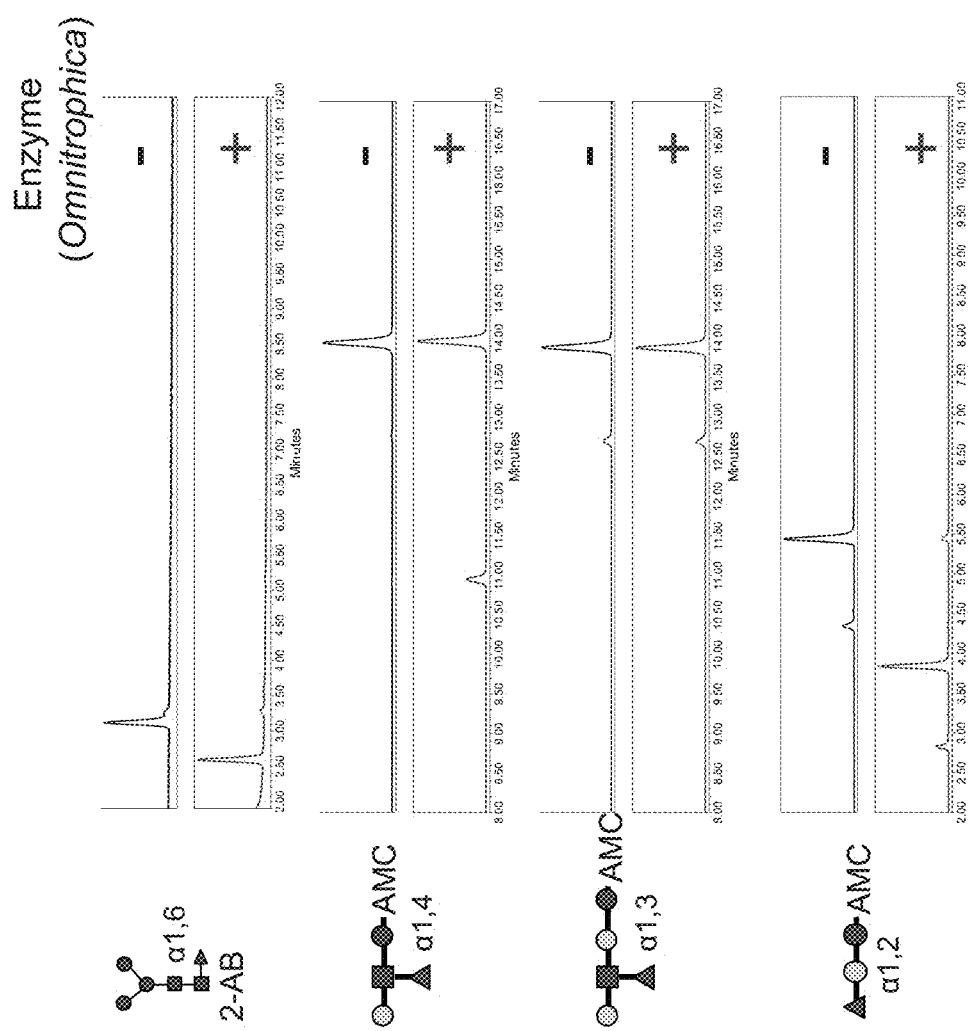

FIG. 9 shows the activity of purified *Omnitrophica* fucosidase on different coumarin-labeled oligosaccharides or 2-AB labeled (M3N2F) N-glycan substrates. The results show that *Omnitrophica* fucosidase is active on α(1,6)-, α(1,2)- and α(1,4)-linked fucose, but has no activity on α(1,3)-fucose.

Figure 10:
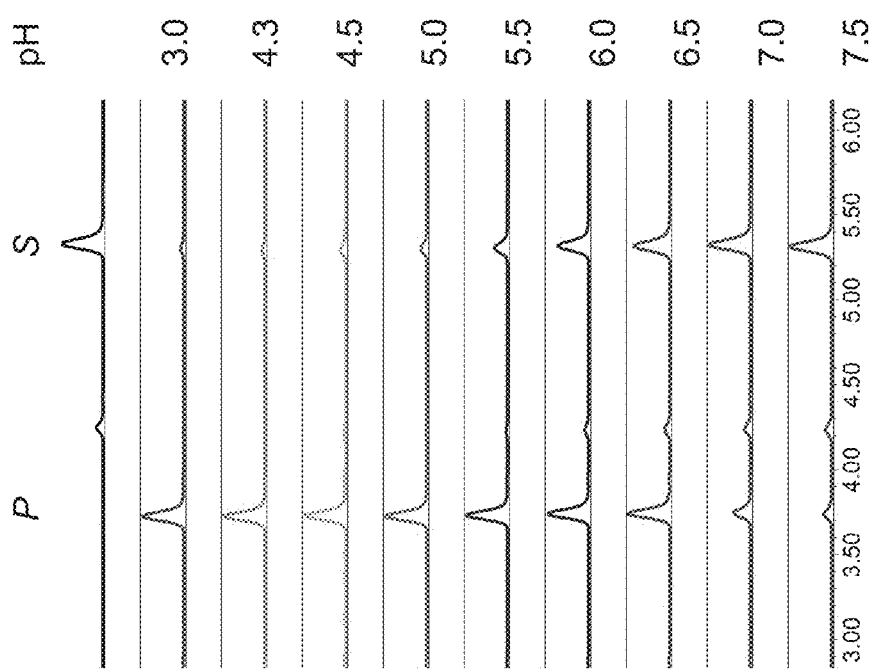

FIG. 10 shows an activity assay using purified *Omnitrophica* fucosidase and 2'-Fucosyllactose-AMC glycan in buffers of varying pH values ranging from pH 7.5-pH 3.0. Peaks are labeled: S (substrate); and P (product). Optimal activity was observed at a pH below 5.5 and as low as pH 3.0.

Figure 11:
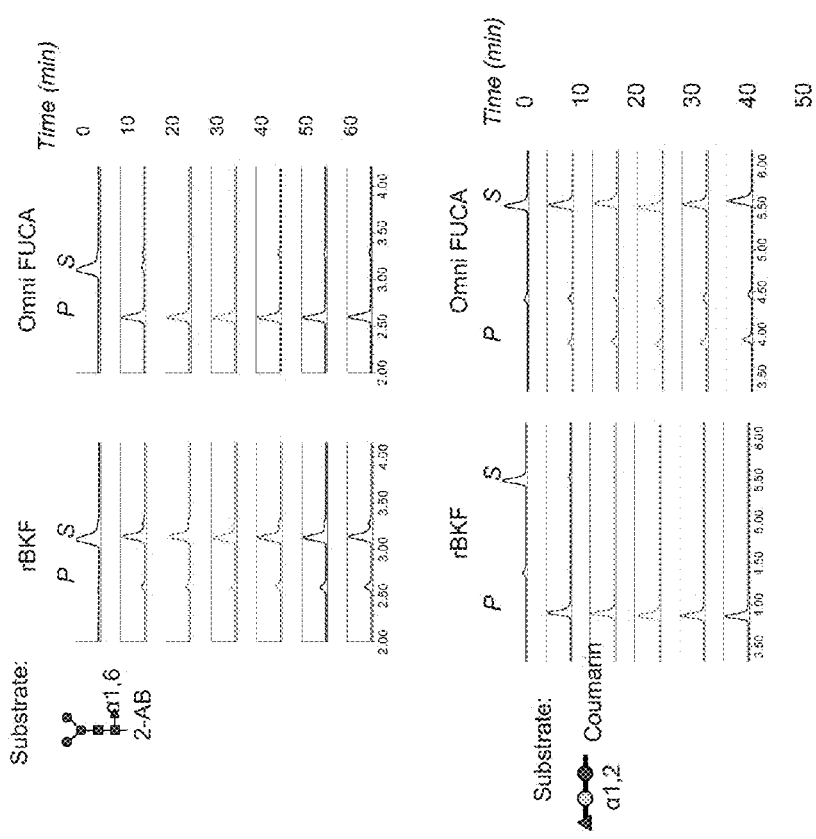

FIG. 11 shows that the glycosidic bond preference of recombinant BKF and *Omnitrophica* fucosidases are different. *Omnitrophica* fucosidase cleaves the core α(1,6)-fucose specifically and very rapidly (within less than 10 minutes) from N-glycans which was labeled using conventional Schiff base labels such as 2-AB (peaks are labeled: S (substrate); and P (product)).

Figure 12:
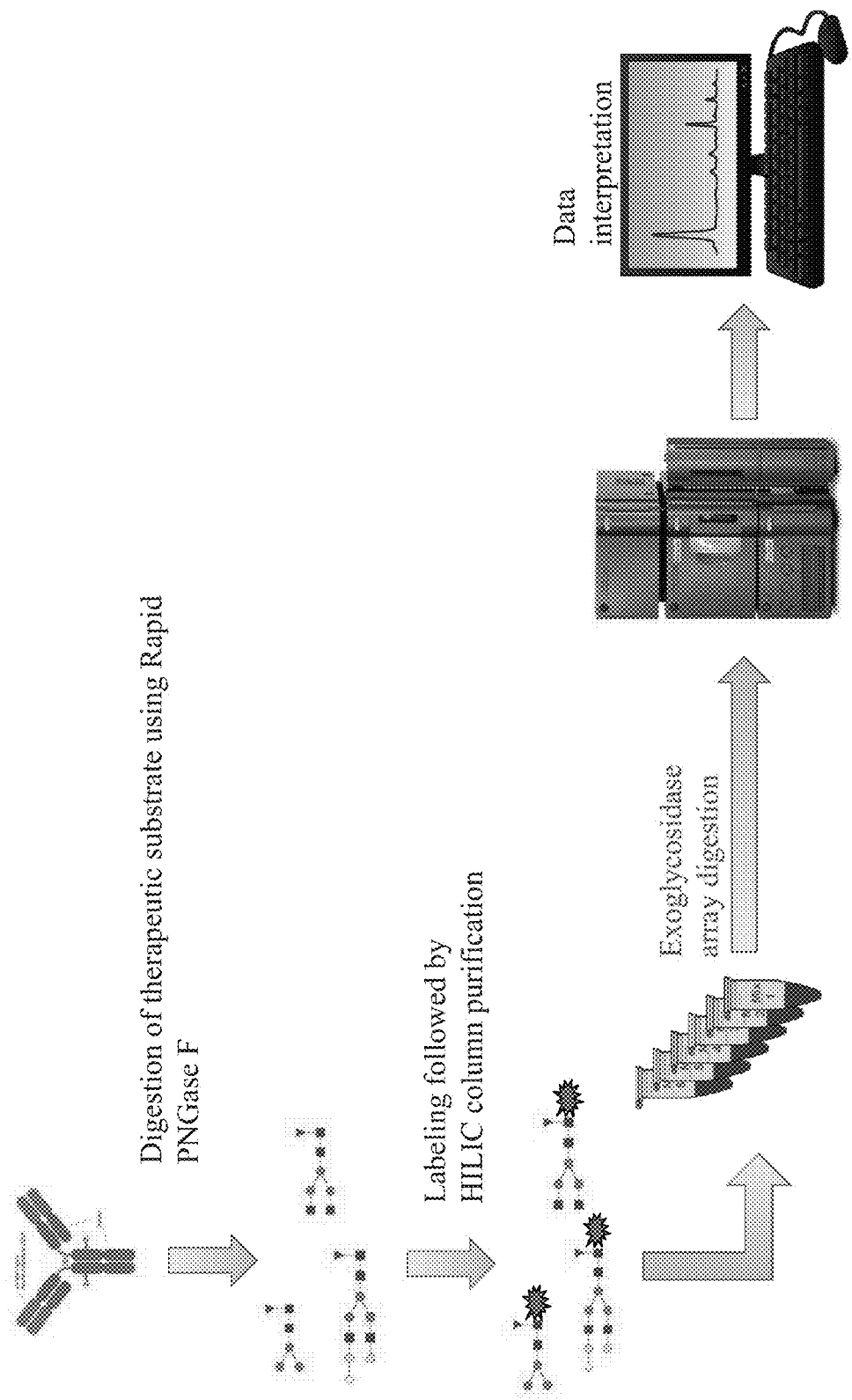

FIG. 12 shows an example of a conventional workflow with fucosidase O for exo-array digestion of glycans from antibodies.

Figure 13:
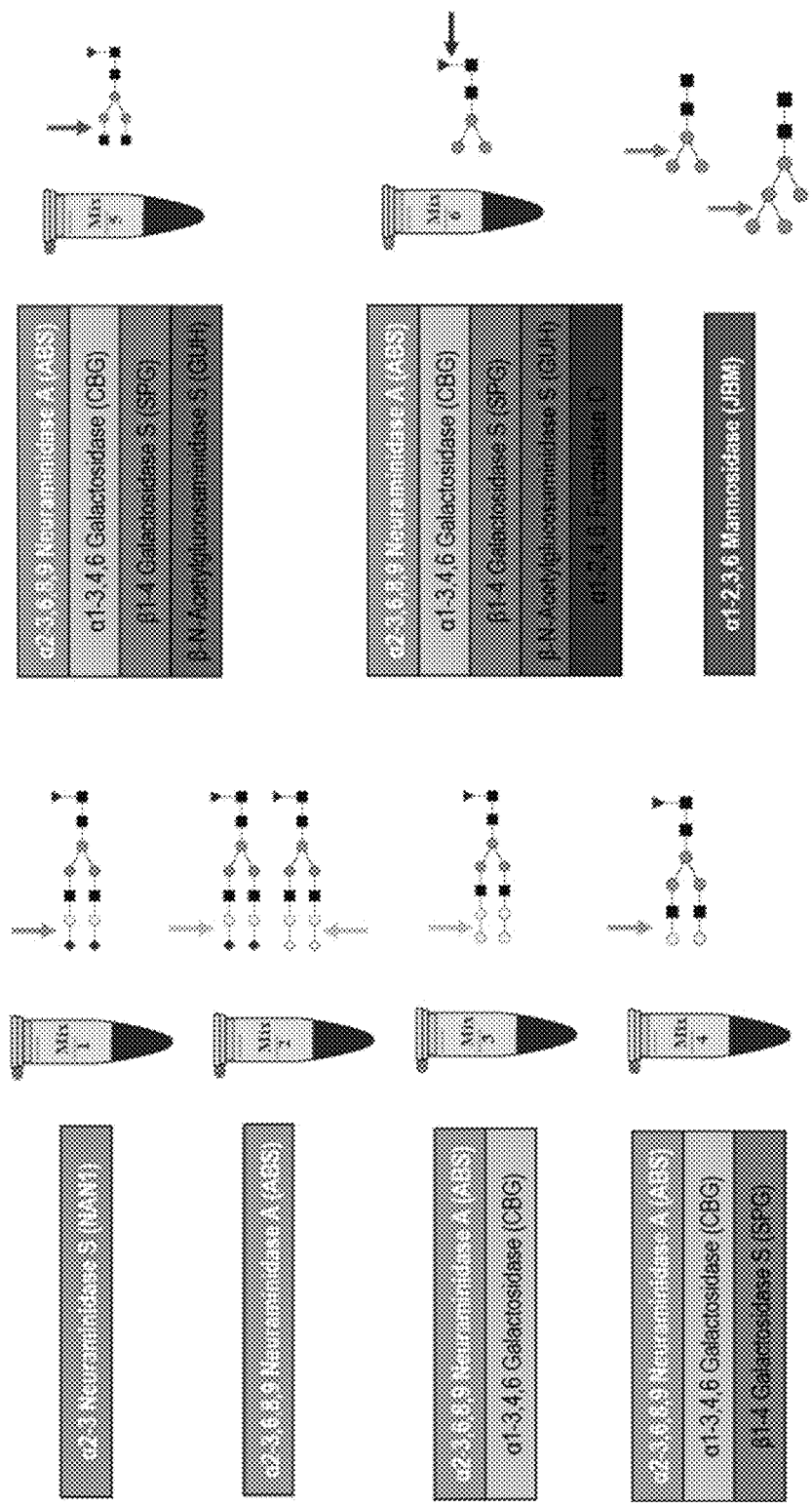

FIG. 13 shows the composition of an exemplary exoglycosidase array with fucosidase O for sequencing antibody N-glycans.

Figure 14A:
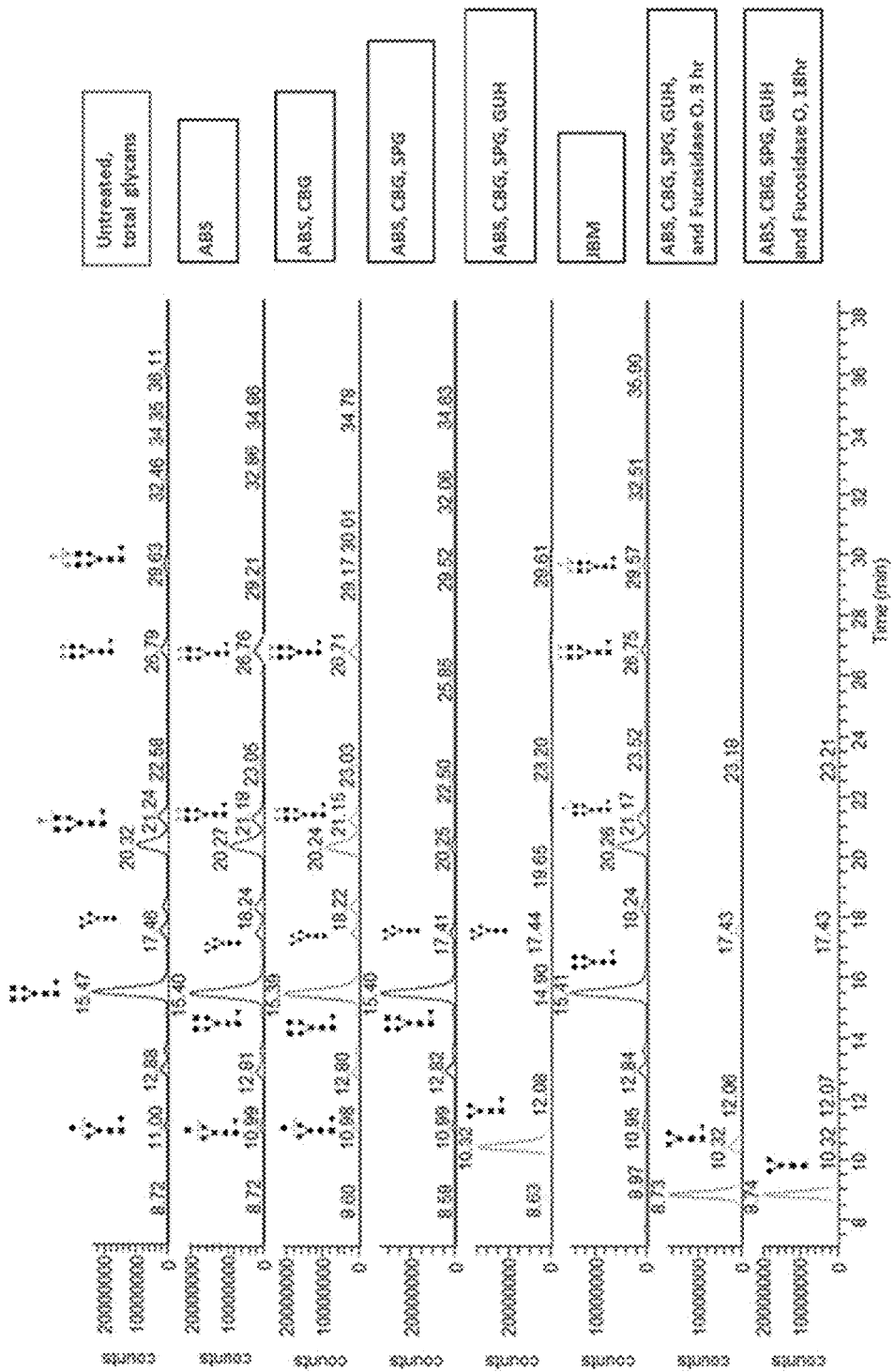
Figure 14B:
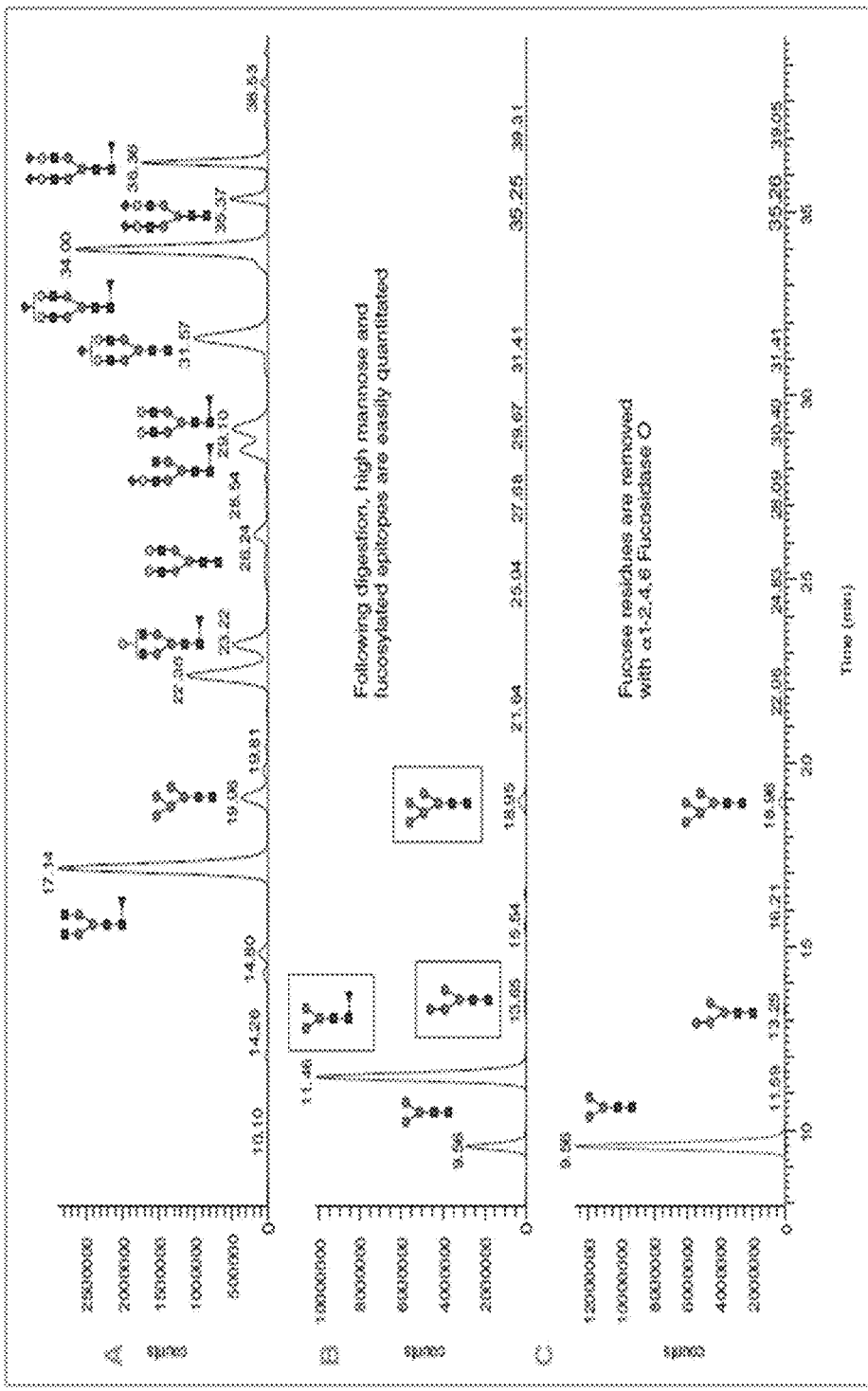

FIG. 14A-14B shows on example of how arrays of exoglycosidases (see FIG. 13) are used to sequence N-glycans (here using Schiff base labeled procainamide conjugated to N-glycans).

FIG. 14A shows the results of the use of the exemplary exoglycosidase array for analyzing antibody glycans (mouse antibody).

FIG. 14B(i)-(iii) shows how the overall level of fucosylation and high mannose structures in glycans released from Enbrel® (Immunex Corporation, Thousand Oaks, Calif.), can be quantitated after trimming to the trimannosyl core with exoglycosidases.

FIG. 14B(i) shows a total glycan profile.

FIG. 14B(ii) shows products resulting from digestion of Enbrel with 2 μl of α2-3,6,8,9 Neuraminidase A, 1 μl of β1-4 Galactosidase S, and 1 μl of β-N-Acetylglucosaminidase S where high mannose and fucosylated epitopes are easily quantified.

FIG. 14B(iii) shows products resulting from Enbrel glycan digetion with 2 μl of α2-3,6,8,9 Neuraminidase A, 1 μl of β1-4 Galactosidase S, 1 μl of β-N-Acetylglucosaminidase S, and 2 μl of α1-2,4,6 Fucosidase O where fucose residues are removed with the α1-2,4,6 Fucosidase O.

Figures 15A, 15B:
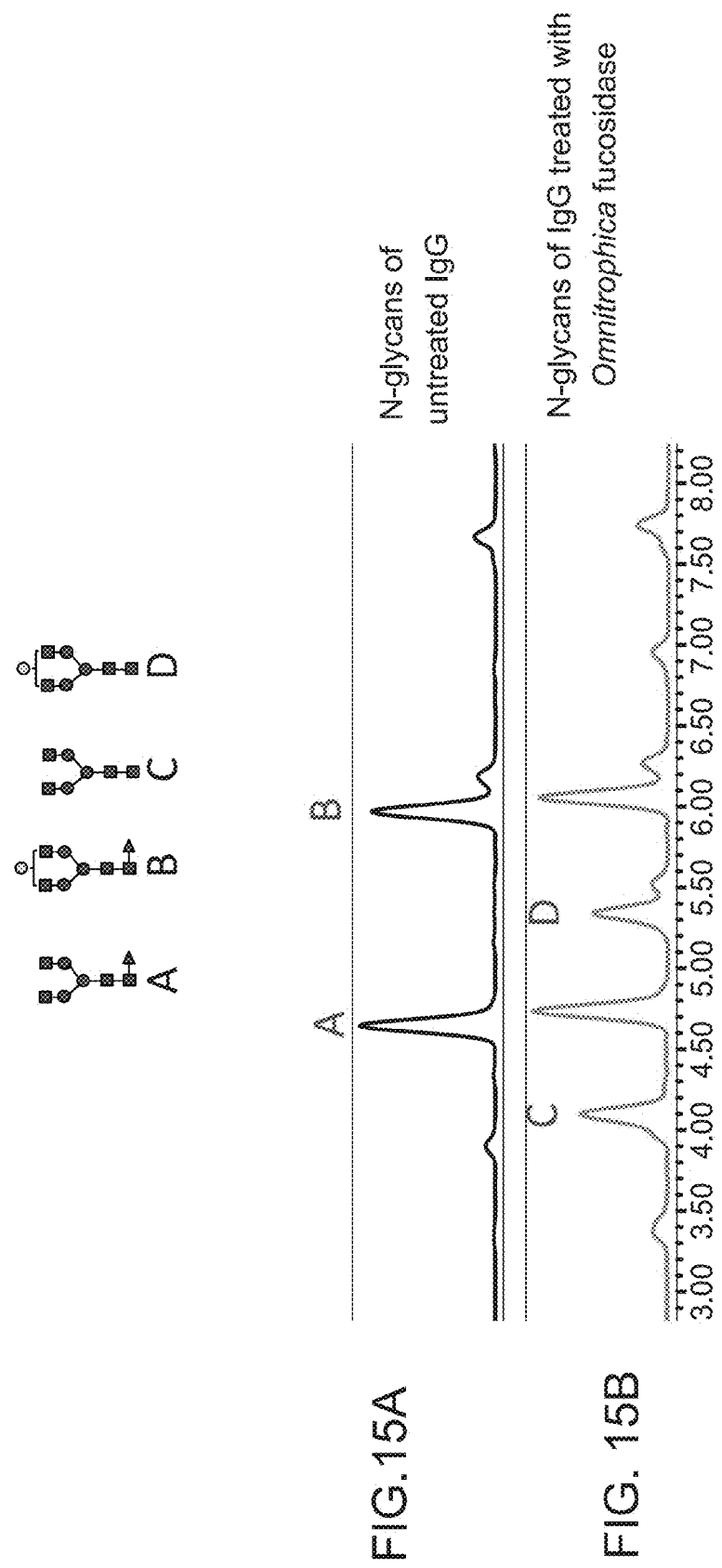

FIG. 15A and FIG. 15B show release of the core fucose from the complex glycans covalently attached to a glycoprotein (murine IgG) where the complex glycans have not been previously modified by reagent enzymes in vitro.

FIG. 15A shows data from UPLC-HILIC-FLR with peaks A and B corresponding to the complex fucosylated glycans covalently attached to the anti-MBP monoclonal antibody (murine IgG2a) under non denaturing conditions.

FIG. 15B shows data from UPLC-HILIC-FLR with peaks C and D after treatment with *Omnitrophica* fucosidase under otherwise similar conditions as FIG. 15A where α(1,6)-linked core fucose has been liberated from the complex N-glycans covalently attached to glycoprotein.

FIG. 16A-D shows substrate specificity and glycosidic bond preference of recombinant fucosidase O. Each oligosaccharide substrate (14 pmol) was mixed with fucosidase O or BKF (1.5 U/mL and 0.085 U/mL final concentration, respectively), and the reaction mixes were incubated at 37° C. Aliquots were taken at each time point and glycans were analyzed by UPLC-HILIC-FLR. The chromatograms were integrated to measure the peak areas of the resulting glycans, and the percentage of fucose removal was calculated. Open squares indicate the glycans treated with fucosidase O; black diamonds indicate the glycans treated with BKF.

Figure 16A:
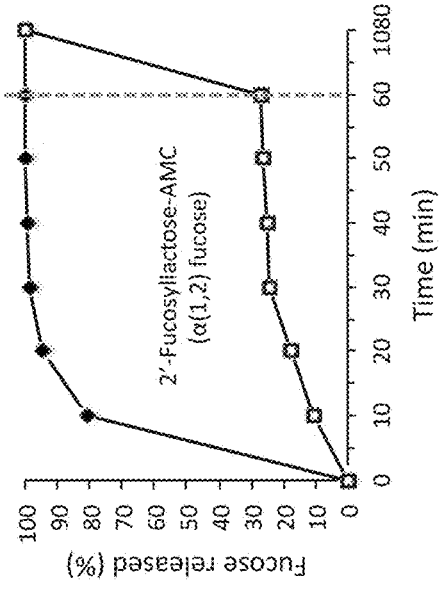

FIG. 16A shows NA2F-2-AB α(1,6) fucose.

Figure 16B:
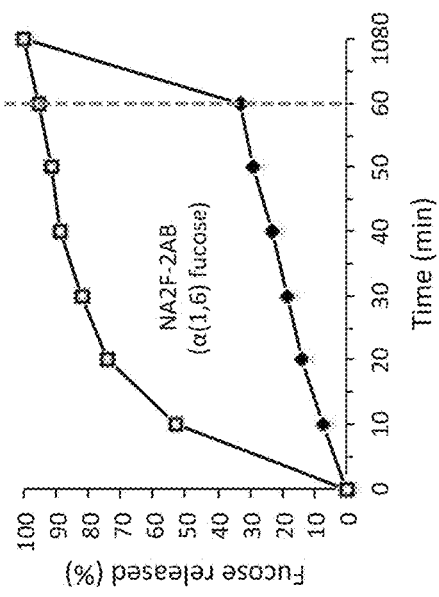

FIG. 16B shows 2'-Fucosyllactose-AMC (α(1,2) fucose).

Figure 16C:
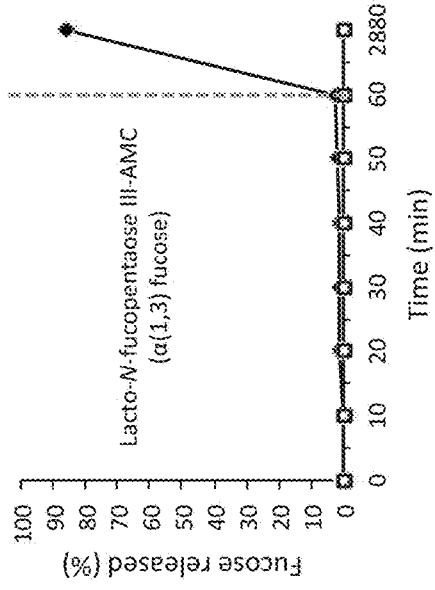

FIG. 16C shows Lacto-N-fucopentaose II-AMC (α(1,4) fucose).

Figure 16D:
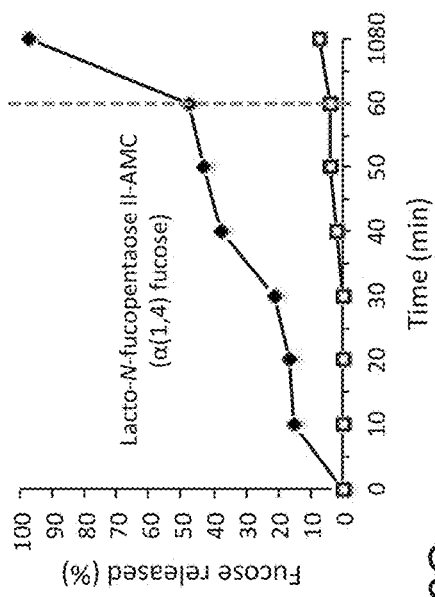

FIG. 16D shows Lacto-N-fucopentaose III-AMC (α(1,3) fucose).

Figure 17:
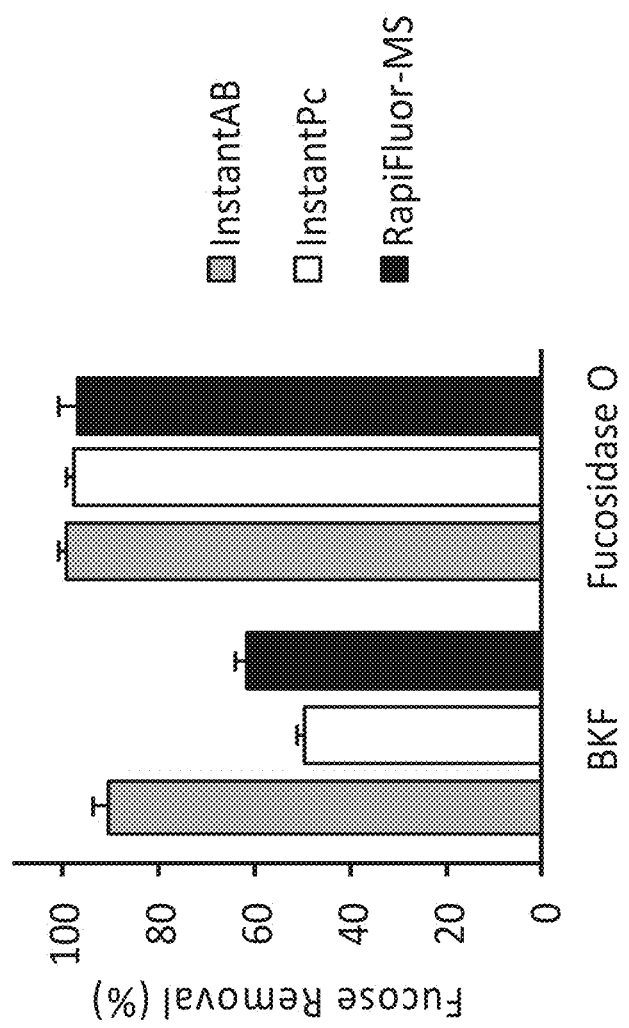

FIG. 17 shows core fucose removal from glycans labeled with different NHS-carbamate labels. Each of N-glycan standard (2 pmol of NA2F-InstantAB, NA2F-InstantPC and NGA2F-RapiFluor-MS) was incubated with fucosidase O (35 U/mL) or BKF (2 U/mL) at 37° C. for 16 hours. The glycans were analyzed by UPLC-HILIC-FLR. The chromatograms were integrated to measure the peak areas of the resulting glycans, and the percentage of fucose removal was calculated.

FIG. 18 A-C shows defucosylation of different complex N-glycans of human IgG labeled with RapiFluor-MS. Labeled N-glycans (8 pmol) were incubated with fucosidase O (35 U/mL) or BKF (2 U/mL) at 37° C. for 16 hours. After treatment, the glycans were analyzed by UPLC-HILIC-FLR.

FIG. 18A shows the results with no enzyme.

FIG. 18B shows the results with fucosidase O.

FIG. 18C shows the results with BKF.

DESCRIPTION OF EMBODIMENTS

Unless defined otherwise herein, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

All patents and publications, including all sequences disclosed within such patents and publications, referred to herein are expressly incorporated by reference. Numeric ranges are inclusive of the numbers defining the range. Unless otherwise indicated, nucleic acids are written left to right in 5' to 3' orientation; amino acid sequences are written left to right in amino to carboxy orientation, respectively. The headings provided herein are not limitations of the various aspects or embodiments of the invention. Accordingly, the terms defined immediately below are more fully defined by reference to the specification as a whole. Unless described otherwise, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Markham, THE HARPER COLLINS DICTIONARY OF BIOLOGY, Harper Perennial, N.Y. (1991) provide one of skill with the general meaning of many of the terms used herein. Still, certain terms are defined below for the sake of clarity and ease of reference.

In one embodiment, analysis of the N-glycan composition of a glycoprotein occurs after cleaving the N-glycan from the glycoprotein using an enzyme (e.g., PNGase F). The reducing end of the N-glycan (i.e., the end that was attached to the protein) may then be labeled for example, by linking a fluorescent label to produce a conjugate. Following column purification of the labeled conjugate, exoglycosidase digestion follows either using single enzymes or arrays. The N-glycan labeled at the reducing end is referred to herein as a conjugate. The conjugate may then be digested with one or more exoglycosidases that have cleavage specificity for terminal glycosidic bonds of specific sugars. The result of the exoglycosidase reaction is removal of the sugar from the non-reducing ends of the N-glycan. This changes the properties of the conjugate. The released sugars and/or the remaining labeled N-glycan can be analyzed quantitatively by an analytical technique such as liquid chromatography (LC), capillary gel electrophoresis, mass spectrometry or LC-MS or the combination of LC-MS, CE-MS, etc. For example, this approach can be used to detect cleaved core α(1,6) fucose and/or the cleaved N-glycan after treating with α-fucosidase.

Because each exoglycosidase has a defined specificity for a certain type of sugar, its stereochemical form (alpha or beta) and the specific site of its attachment to its adjacent sugar, exoglycosidase treatment yields structural information about the N-glycan. For example, treatment of an N-glycan that contains core α(1,6) fucose with α-fucosidase causes removal of the fucose and a diagnostic shift in the N-glycan's chromatographic mobility that confirms the presence of this sugar.

Figure 3:
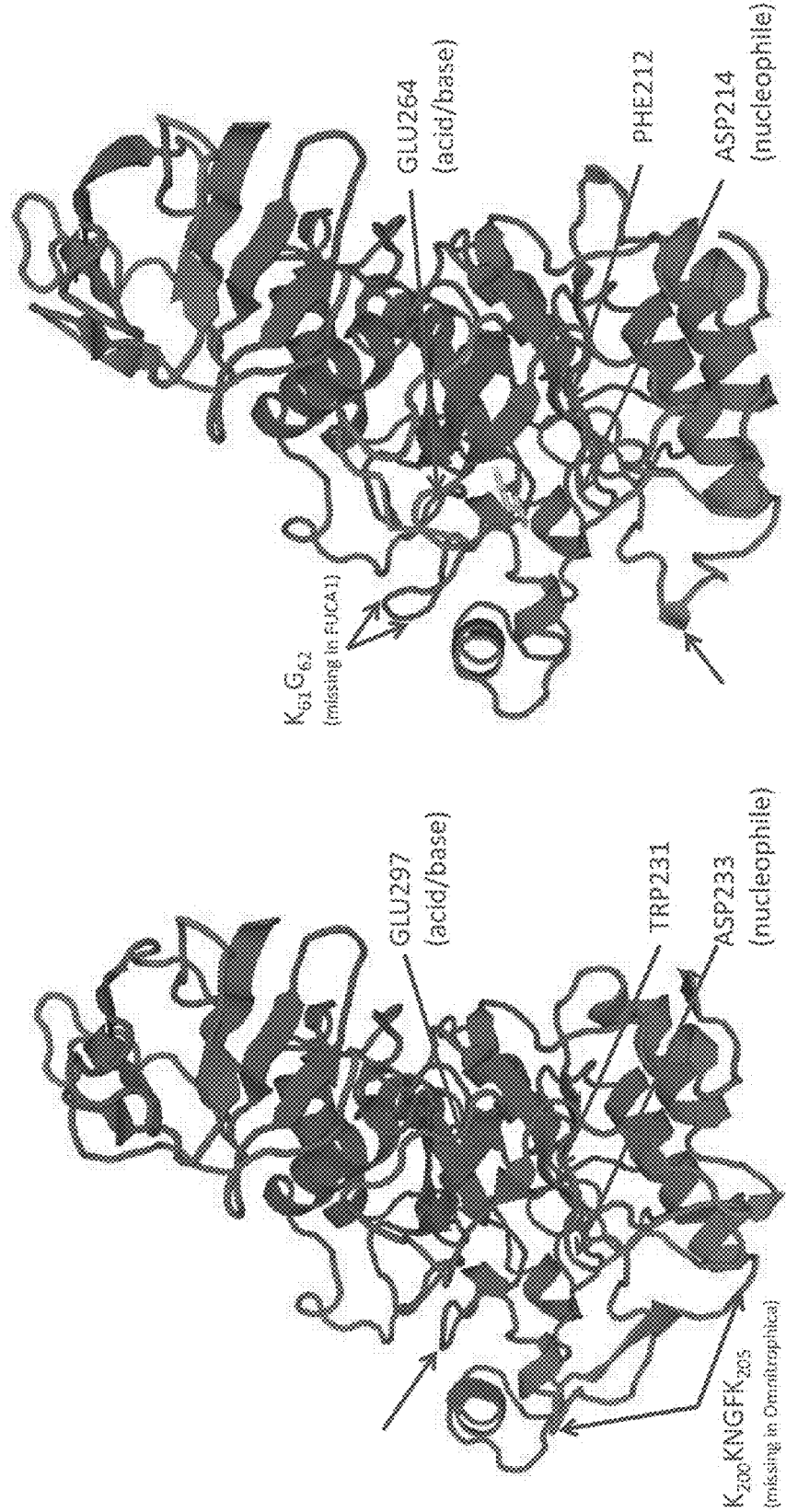
FIG. 3 shows a tertiary structure models of bovine FUCA1 (BKF) and *Omnitrophica* α-L-fucosidase created by SWISS-MODEL using a structure of *Thermotoga maritima* α-L-fucosidase as a template. For the *Omnitrophica* enzyme, the location of catalytic acid/base in the mobile loop (GLU264), as well as other differences indicated in the figure are believed to correlate with the differences in substrate recognition between these enzymes.
Figures 4A, 4B, 4C, 4D:
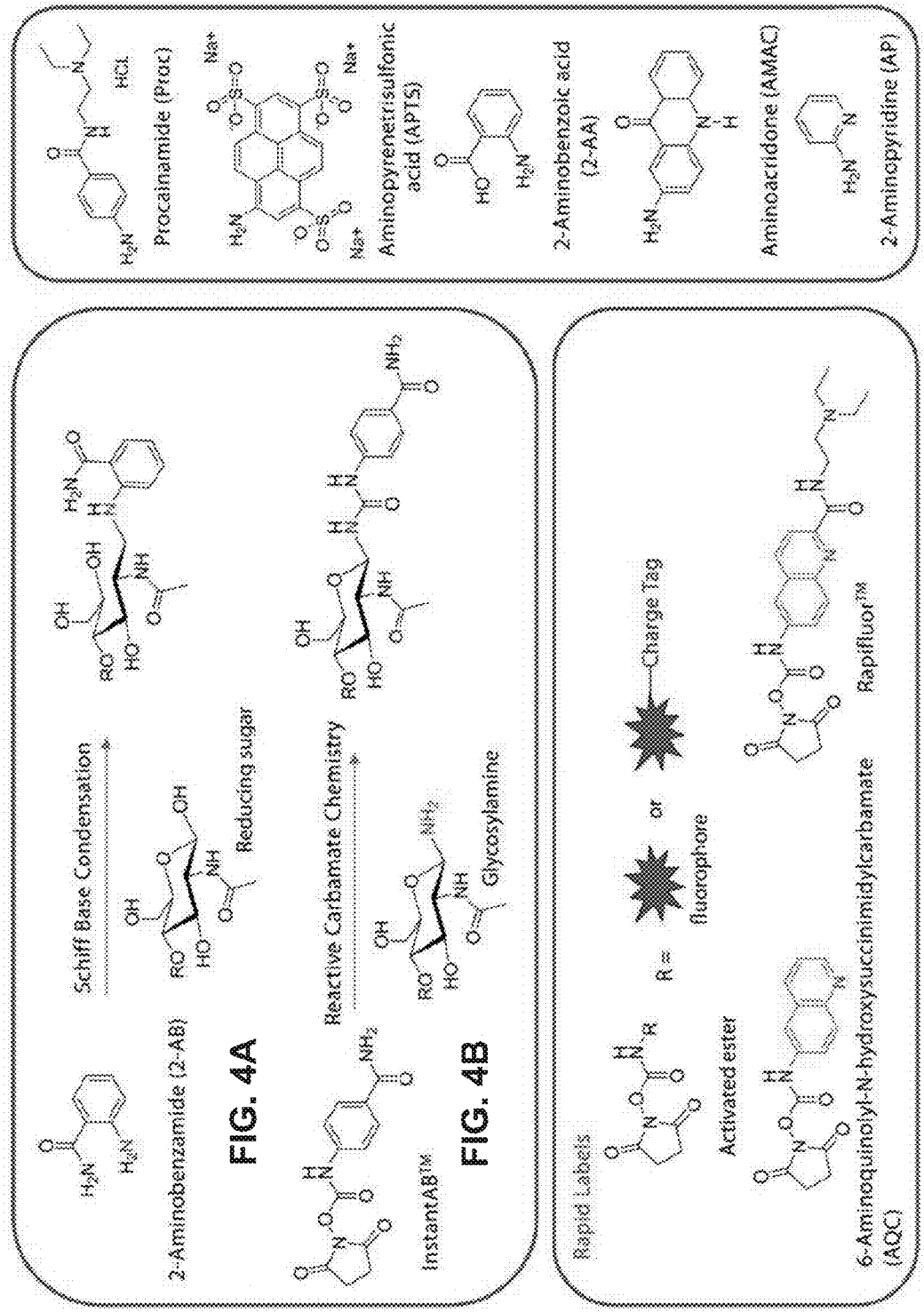
FIG. 4A-4E show different types of labeling of N-glycan.
Figure 4E:
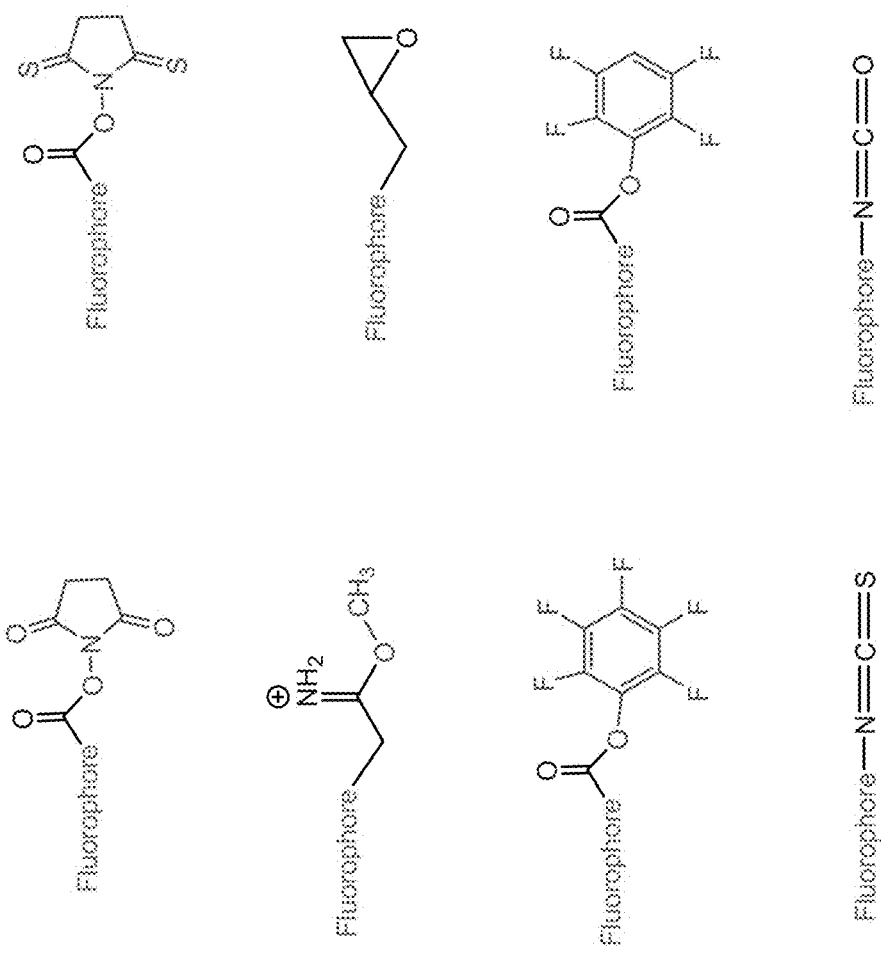
Figure 5:
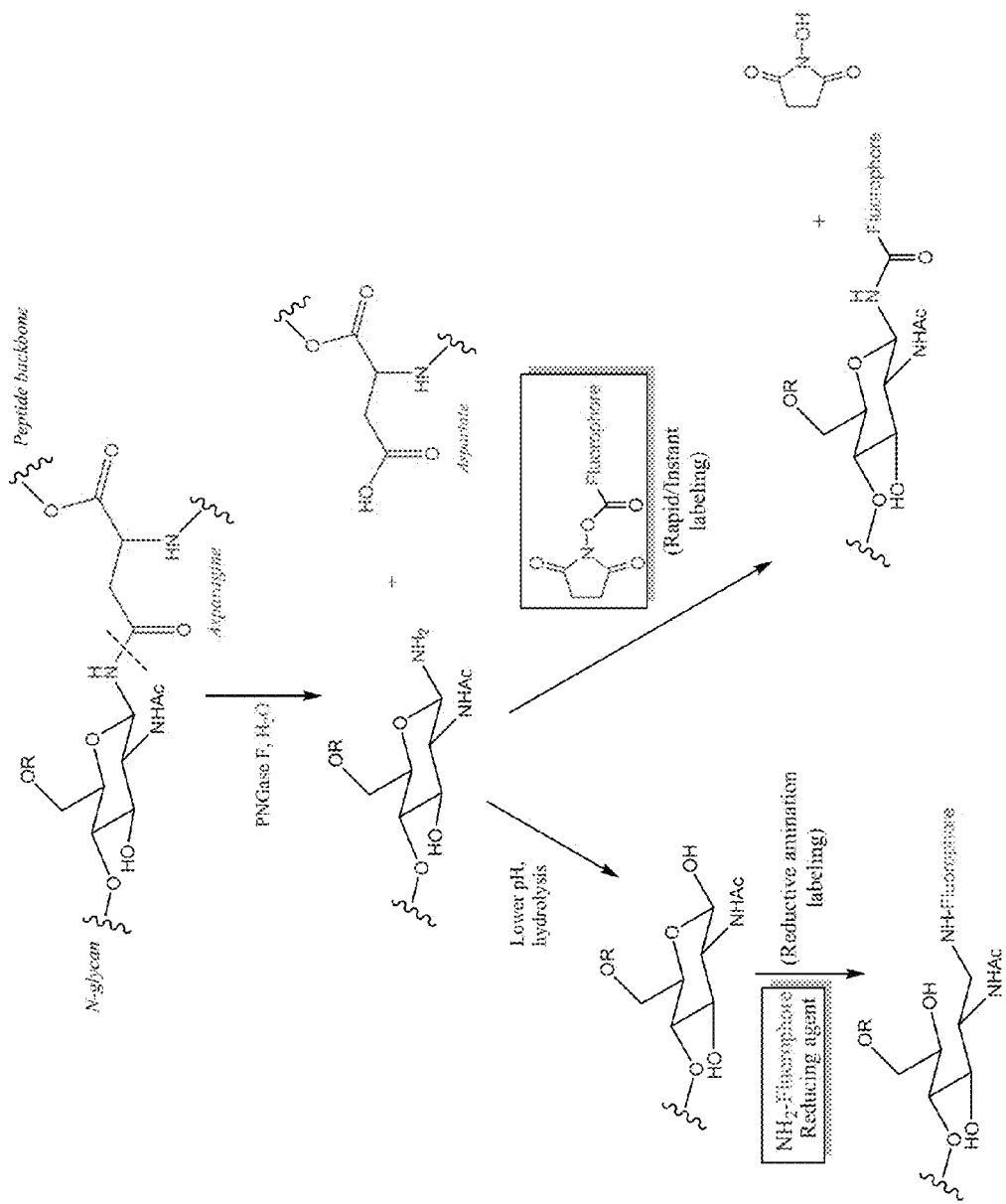
FIG. 5 shows two alternative labeling methods of the enzymatically released N-glycans. The N-glycan can be cleaved from a glycoprotein using PNGase F. The released N-glycan can be subjected to low pH and linked to a fluorophore via a Schiff base condensation reaction and reduction (shown on the left) or via an amine reactive chemistry (shown on the right).

To exemplify various aspects of embodiments, FIGS. 1-3 show details of fucosidase O compared to other fucosidases. This includes sequence comparisons that highlight differences of note between the prokaryotic fucosidase O and mammalian fucosidases that may correlate with functional differences. Structural comparisons are provided in FIG. 3, which also show how the 3D structure may permit the fucosidase O to react with conjugates having carbamide bonds where BKF fucosidase is substantially inactive. FIGS. 4A-4E, and FIG. 5 show details of the substrate chemistry that places a label or tag onto the reducing end of an N-glycan. Examples of the interaction of various fucosidases with various substrates under conditions specified in the description of figures and the examples are shown in FIGS. 6-11 and FIG. 15A-15B. Standard sequencing workflows are shown in FIGS. 12-14B.

As used herein, the term "label" refers to a non-naturally occurring detectable moiety that facilitates detection of the entity to which it is joined. For example, a label may be optically detectable and, as such, may contain a chromophore or a fluorophore. In other embodiments, the label may contain a mass tag or a charge tag (i.e., a tag of known charge that can be detected in mass spectrometry) or the like. In some embodiments, a label may contain a fluorophore and a charge tag.

Schiff base chemistry has been traditionally used to attach these labels to the reducing end of N-glycans. In this reaction, an amine functionalized label reacts in a condensation reaction with the aldehyde group of the glycan, resulting in a Schiff base, which can be reduced to yield amide bond. This labeling chemistry leaves the sugar ring open (FIG. 4A-4E, FIG. 5). In addition to being a relatively slow reaction, other disadvantages include toxicity of reagents and incomplete reaction steps following Schiff base formation.

Recently, a new generation of labels has been developed that significantly improve the speed of glycan labeling and the sensitivity in certain detection methods (e.g. liquid chromatography and/or mass spectrometry). These labels include AQC (Cohen, 1993), RFMS (WO 2013049622), InstantAB (US 2012/0107942), InstantPC (US 2012/0107942) and Instant APTS (US 2012/0107942). These labels can be attached to the reducing end of an N-glycan using reactive carbamate chemistry to form a carbamide linkage with the N-glycan. This chemistry fluorescently labels the reducing end GlcNAc, but leaves its ring closed (FIG. 4A-4E, FIG. 5).

Carbamate chemistry also referred to herein as activated ester chemistry or reactive carbamate chemistry or NHS-carbamate chemistry refers to a chemical reaction in which an alkoxy or aryloxy group of an ester that contains a fluorophore serves as the leaving group, while the primary amine of the glycosylamine from the sugar serves as the nucleophile. The end result is the sugar is attached to the fluorophore through an amide bond or other bonds. Carbamate chemistry also encompasses reactions where the reactive group on the fluorophore is an epoxy, isothiocyanate, or isocyanate. Carbamate chemistry is utilized by dyes RFMS (Lauber, et al., Annal Chem, 87, 5401-5409, 2015), InstantAB, InstantPC, and AQC (Cohen, 1993); Stockmann, et al., Anal Chem, 87:8316-8322, 2015). This strategy significantly improves labeling speed, and the tertiary amines present on InstantPC and RFMS can also enhance the sensitivity of glycan detection in mass spectrometry applications (Lauber, 2015). Examples of exoglycosidases that have specificity for certain monosaccharide linkages and anomericity ($\alpha/\beta$) and are used in N-glycan analysis involving Schiff base labeled conjugates include $\alpha$2-3 neuraminidase S, $\alpha$2-3,6,8,9 neuraminidase A, $\alpha$1-3,4,6 galactosidase, $\beta$1-4 galactosidase, $\beta$-N-acetylglucosaminidase S, $\alpha$1-2,3,6 mannosidase; $\alpha$-N-Acetylgalactosaminidase; $\alpha$1-3,4 Fucosidase; P—N-Acetylhexosaminidase; $\beta$1-3 Galactosidase (New England Biolabs, Ipswich, Mass.) and other commercially available exoglycosidases. FIG. 13 shows an example of a panel of exoglycosidases, although other panels could be used. Common enzymes used for N-glycan sequencing include: *Arthrobacter ureafaciens* sialidase (ABS), almond meal alpha fucosidase (AMF), bovine testes beta galactosidase (BTG), coffee bean alpha galactosidase (CBG), *Streptoccous pneumoniae* beta hexosaminidase (SPH), jack bean alpha mannosidase (JBM), *Streptoccous pneumoniae* beta neuraminidase (NAN1), *Streptoccous pneumoniae* beta galactosidase (SPG), *Helix pomatia* beta-mannosidase, *Aspergillus saitoi* alpha-mannosidase and BKF that is preferably replaced by fucosidase O for the reasons give herein.

After substantial screening of fucosidases, a prokaryotic fucosidase was identified that was found to be more effective in cleaving fucose on complex N-glycans than previously preferred eukaryotic fucosidases. This fucosidase has an amino acid sequence that is at least 80% identical to (e.g., at least 90%, at least 95% or 100% identical to) amino acids 23-359 of sequence of SEQ ID NO:1, the wild type *Omnitrophica* OLB16 $\alpha$-fucosidase (as shown in FIG. 1). This part of SEQ ID NO:1 contains the catalytic domain based on sequence alignments with other fucosidases (FIG. 2) and structural analysis (FIG. 3) (also see EC 3.2.1.127 using IUBMB enzyme nomenclature). In some embodiments, the enzyme may have an amino acid sequence that is at least 80% identical to (e.g., at least 90%, at least 95% or 100% identical to) amino acids 23-449 of SEQ ID NO:1.

However as discussed further below, this glycosidase functionally differs in its catalytic properties from BKF and other eukaryotic fucosidases. This fucosidase has a preference for cleaving an $\alpha$ (1,6) linkage over cleavage of other glycosidic linkages such as in $\alpha$(1,2)- and $\alpha$(1,4) between an $\alpha$-L-fucose and an N-acetyl-D-glucosamine in an N-glycan (see for example, FIG. 11). The $\alpha$-fucosidase of the bacterium *Omnitrophica* OLB16 rapidly cleaves core $\alpha$(1,6) linked fucose from N-glycans that have been labeled with new generation labels via a carbamide linkage. This enzyme has a pH optimum between pH 3 and pH 5 (see for example, FIG. 10). In one embodiment, the reaction mix containing a fucosidase and one or more other enzymes has pH 3.0-pH 5.5.

The *Omnitrophica* $\alpha$-fucosidase and variants thereof may be used herein as a single reagent in a buffer, a component in an enzyme mixture or a component in a reaction mix containing a glycoprotein/peptide/N-glycan where one or more additional exoglycosidases may be additionally added. These additional exoglycosidases may be selected from any of exoglycosidases described above. A plurality of exoglycosidases can be used in serial digests of N-glycans or in arrays of enzyme mixtures (see for example, FIG. 13 showing standard exoglycosidase panels for sequencing of N-glycans from mouse antibody). In some embodiments, one or more neuraminidases or exoglycosidases were expressed in a prokaryotic expression system or in eukaryotic expression systems. An advantage of recombinant exoglycosidases over naturally occurring purified exoglycosidases includes the absence of N-glycans on the recombinant enzymes that might confuse analysis of the target glycoprotein or peptide.

In general, exoglycosidase reactions can be performed on N-glycans that have been labeled using a Schiff base condensation reaction. These reactions take place under conditions that are compatible with enzyme activity. For example, pH, temperature, reaction solution components and concentration (e.g., salt, detergent, etc.), and length of reaction time can be optimized in order to achieve a desired level of exoglycosidase activity. In some embodiments, simultaneous digestion with multiple exoglycosidases can be used to analyze glycan structure and/or function. In some cases, simultaneous digestion can be performed in order to determine the presence of particular types of linkages and/or glycan modifications.

The fucosidase O and variants thereof has been found to have improved properties over the commercial BKF that does not cleave or inefficiently cleaves fucose on an N-glycan if the N-glycan is labeled with a dye using carbamate chemistry. While not wishing to be limited by theory, it is thought that the carbamate linkage produced by the reaction of the reactive carbamide of the label and the amine of the N-glycan results in a "closed ring" form of the labeled GlcNAc that impedes the BKF. In addition or alternatively, the molecular size, structure and/or charge of the label may be responsible for the observed differences in enzyme recognition of substrate and/or kinetics for different fucosidases. The identification of improved properties of fucosidase O greatly facilitates the use of the new generation of labels for many analyses, including exoglycosidase-based glycan sequencing and other applications in which the new generation of labels are used. Glycans labeled with "instant" labels that utilize reactive carbamate chemistry may be incubated with fucosidase for as much as 18 hours. In one embodiment, the incubation may be less than 18 hours, for example less than 15 or 12 or 8 or 6 or 4 or 2 or 1 hour.

In addition, fucose cleavage from N-glycan labeled molecules that utilize Schiff base chemistry has been greatly improved using fucosidase O and variants thereof because of the improved kinetics of the reaction can be completed in minutes instead of many hours thus accelerating analysis (e.g. sequencing). Embodiments include combining an $\alpha$-fucosidase with a conjugate comprising an N-glycan and a label, to make a reaction mix, and incubating the reaction mix so as to cleave any core fucose from the N-glycan. The reaction may be completed in less than a few minutes (e.g., less than 1 hour, 30 minutes, 10 minutes or 5 minutes) when the N-glycans are labeled by means of Schiff Base chemistry (e.g., 2-AB).

Another advantage of fucosidase O and variants thereof is the ability for the first time of removing a fucose (e.g., a core fucose is an $\alpha$(1,6)-linked fucose residue that is attached to the N-acetyl glucosamine moiety that is linked to asparagine on the protein) from an N-glycan (core N-glycan or complex N-glycan) in otherwise intact glycoprotein or peptide without any prior total or partial deglycosylation steps (an intact protein) to produce an engineered molecule. In preferred embodiments, core α(1,6) fucose may be removed from intact or complex N-glycans on mammalian immunoglobulins (FIG. 15A-15B), a capability that BKF and other fucosidases lack. The ability to engineer glycoproteins has been found to be important in the pharmaceutical industry where the composition of glycans on biotherapeutics can affect their performance or their rate of clearance from the bloodstream. For example, various studies have demonstrated that certain antibodies having N-glycans at Asn-297 that lack core α(1,6) fucose are able to bind to the FcgRllla receptor with higher avidity than core fucosylated N-glycans. This stronger interaction enhances the antibody dependent cellular cytotoxicity (ADCC) response (Ferrara, et al., Biotechnol. Bioeng., 93:851-861, 2006; Ferrara, et al., Proc. Natl. Acad. Sci. U.S.A., 108:12669-12674, 2011). Existing enzymatic strategies first remove the bulk of an N-glycan by digestion with endoglycosidases such as endo S, endo F1, endo F2, endo H, or cocktails of these enzymes leaving a single GlcNAc residue to which core fucose is attached. This fucose can be accessed and removed by commercial fucosidases followed by glycoengineering back the other removed sugars (Collin, et al., EMBO J., 20:3046-3055, 2001; Li, et al., J. Biol. Chem., 291:16508-16518, 2016; Tsai, et al., ACS Chem. Biol., 12:63-72, 2017; and WO 2015/184008).

The term "complex N-glycan" as used here and in the claims refers to an N-glycan containing core sugars and also extra sugars. The term "intact" as used herein and in the claims refers to a naturally occurring N-glycan covalently linked to a protein or peptide. An intact N-glycan is intended to mean that it has not been previously enzymatically modified in vitro meaning it has not been cleaved or truncated by reagent enzymes in a reaction mix.

In certain embodiments, a kit may comprise: (a) the α(1,6)-fucosidase and (b) an amine-reactive label, as discussed above and shown by example in FIG. 4E. The various components of the kit may be present in separate containers or certain compatible components may be pre-combined into a single container, as desired. In addition to the fucosidase, the kit may contain any of the additional components used in the method described above, e.g., a buffer, etc. In some embodiments, the kit may further comprise an enzyme for cleaving N-glycans off glycoproteins, e.g., PNGase F. In some embodiments, the kit may further comprise one or more exoglycosidases or mixtures of exoglycosidases in addition to the fucosidase, as listed above. In these embodiments, at least one of the one or more exoglycosidases may combined with the α(1,6)-specific fucosidase in an enzyme mixture, e.g., an enzyme mix described above. The amine-reactive label may contain an activated carbamate, although, as shown in FIG. 4A-4E and FIG. 5, other chemistries may be used.

In addition to above-mentioned components, kits may further include instructions for using the components of the kit to practice the subject methods, i.e., instructions for sample analysis. The kit may also include components to isolate glycoproteins from culture media or biological samples (such as Protein A beads) and cartridges or plates that can purify labeled or unlabeled glycans.

Methods in accordance with the disclosure can be applied to glycans obtained from a wide variety of sources including, but not limited to, therapeutic formulations (e.g., antibodies erythropoietin, insulin, human growth hormone, etc.), commercial biological products (e.g., those presented in Table 5 of U.S. Pat. No. 8,729,241), and biological samples. A biological sample may undergo one or more standard analyses and/or purification steps prior to or after being analyzed according to the present disclosure.

In some embodiments, glycans from different batches of a therapeutic glycoprotein, whether prepared by the same method or by different methods, and whether prepared simultaneously or separately, are compared. In such embodiments, the present disclosure facilitates quality control of glycoprotein preparation.

In some embodiments, methods described herein can be used to characterize and/or control or compare the quality of therapeutic products. By way of example, the present methodologies can be used to assess glycosylation in cells producing a therapeutic glycoprotein. Particularly given that glycosylation can often affect the activity, bioavailability, or other characteristics of a therapeutic glycoprotein, methods for assessing cellular glycosylation during production of such a therapeutic glycoprotein are particularly desirable. Among other things, the present disclosure can facilitate real time analysis of glycosylation in production systems for therapeutic proteins.

Representative therapeutic glycoproteins whose production and/or quality can be monitored in accordance with the present disclosure include, for example, any of a variety of hematologic agents (erythropoietin, blood-clotting factors, etc.), interferons, colony stimulating factors, cytokines, antibodies, enzymes, and hormones. The term "glycoprotein" refers to any type of polypeptide that has been glycosylated, including peptides and protein complexes (e.g., antibodies, fusion proteins).

All references cited herein are incorporated by reference.

EXAMPLES

Aspects of the present teachings can be further understood in light of the following examples, which should not be construed as limiting the scope of the present teachings in any way. These examples include descriptions of the cloning, expression and biochemical characterization of an α-fucosidase from *Omnitrophica* bacterium (termed fucosidase O). This fucosidase O has a strong preference for hydrolysis of α(1,6)-linked core fucose over other fucose linkages. The enzyme can also remove α(1,3)-linked core fucose from plant N-glycans. fucosidase O is able to efficiently hydrolyze core α(1,6)-linked fucose from N-glycans labeled with any of the existing NHS-carbamate activated fluorescent labels. Unless stated otherwise, chemical reagents and solvents were purchased from Sigma-Aldrich (St. Louis, Mo.). Labeled N-glycan substrates used for specificity tests and activity assays were obtained from Prozyme (Hayward, Calif.). A standard of human IgG N-glycans labeled with RFMS was obtained from Waters (Milford, Mass.). BKF (GLYCO α(1-2,3,4,6) fucosidase) was from Prozyme. 2-chloro-4-nitrophenyl α-L-fucopyranoside (CNP-Fuc) was obtained from CarboSynth US (San Diego, Calif.).

Example 1: Substrates and Methods for Glycan Labeling and Analysis

I. Substrates
(a) Labeled N-glycans substrates used for specificity tests and activity assays were obtained commercially from Prozyme and Waters as follows:
2-AB-, InstantAB-, and InstantPC-labeled asialo-, galactosylated biantennary, core-substituted with fucose (NA2F-2-AB, NA2F-InstantAB and NA2F-InstantPC, respectively); 2-AB-labeled conserved trimannosyl core substituted with fucose (M3N2F-

2-AB) were from Prozyme; and human IgG N-glycans, RFMS labeled were from Waters.

(b) Labeled oligosaccharides: Lacto-N-fucopentose III, 2'-Fucosyllactose (Prozyme, Hayward, Calif.) and Lacto-N-fucopentose II (Dextra Laboratories, Reading, UK) were labeled with 7-amino-4-methylcoumarin (AMC) as described below. AMC-labeled glycans were cleaned-up using gel filtration on G-25 column.

II. Labeling of Selected Substrates

Schiff base condensation with 2-aminobenzamide (2-AB) (Sigma-Aldrich, St. Louis, Mo.) or 7-amino-4-methylcoumarin (AMC) (Sigma-Aldrich, St. Louis, Mo.) was used to label N-glycans and oligosaccharides as follows:

2-AB labeling mix for labeling N-glycans: 47.6 mg 2-AB in 300 µl glacial acetic acid was mixed with 62.8 mg NaCNBH4 in 700 µl, DMSO (final conc. of 350 mM 2-AB, 1 M sodium cyanoborohydride in 1 ml 7:3 DMSO:AcOH). 10 µl of labeling mix was added per 1 nmol of dried glycans and heated at 65° C. for 2 hours to result in a labeled N-glycan.

7-amino-4-methylcoumarin (AMC) labeling mix for labeling oligosaccharides: 20 mg AMC, 41 µl glacial acetic acid, 35 mg sodium cyanoborohydride (NaCNBH4) and 300 µl methanol. 10 µl of the labeling mix was added per 3 nmol of dried N-glycans. This was heated at 80° C. for 45 minutes to label the N-glycan.

III. Clean-Up of the Labeled N-Glycans Using SPE-HILIC Nest Cartridges (MicroSpin™ columns, 10-100 µg capacity (The Nest Group, Southborough, Mass.)) Cartridges were equilibrated using 350 µl: 1× with acetonitrile (ACN), 2× water, 3×90% ACN/NH$_4$F, 2 minute spins at 110×g (800 rpm). Labeling samples (10 µl) were diluted up to 300 µl with 90% ACN/10% NH$_4$F, loaded on cartridge, and washed with 5×350 µl 90% ACN/NH$_4$F. Samples were eluted in 100 µl 50 mM NH$_4$F, pH 4.4.

IV. Analysis of N-Glycan Labeled Conjutes by Ultra-Performance Hydrophilic Interaction Liquid Chromatography with Fluorescence Detection (UPLC-HILIC-FLR)

Gradients and detection parameters vary according to the labeled substrate. In general, 2-AB labeled N-glycans or InstantAB-labeled N-glycans or InstantPC-labeled N-glycans (obtained according to Example 1 I(a) or as a product of enzyme cleavage of a glycoprotein) or products of exoglycosidase digestion were separated by UPLC using an ACQUITY® BEH glycan amide column (2.1×150 mm, 1.7 µm) on an H-Class ACQUITY instrument (Waters, Milford, Mass.) equipped with a quaternary solvent manager and a fluorescence detector. Solvent A was 50 mM ammonium formate buffer pH 4.4 and solvent B was acetonitrile. The gradient used was 0-1.47 min, 30% solvent A; 1.47-24.81 minutes, 30-47% solvent A; 25.5-26.25 minutes, 70% solvent A; 26.55-32 minutes, 30% solvent A. The flow rate was 0.561 mL/minutes. The injection volume was 10 µL and the sample was prepared in 70% (v/v) acetonitrile. Samples were kept at 5° C. prior to injection and the separation temperature was 40° C. The fluorescence detection wavelengths were: $\lambda$ex=330 nm and $\lambda$em=420 nm for 2-AB; $\lambda$ex=278 nm and $\lambda$em=344 nm for InstantAB, $\lambda$ex=285 nm and $\lambda$em=345 nm for InstantPC. Data collection rate was 20 Hz. All data was processed using Empower® 3 chromatography workstation software (Waters, Milford, Mass.).

In general for RFMS-labeled N-glycans, separation was carried out by UPLC using an ACQUITY BEH glycan amide column (2.1×150 mm, 1.7 µm) on an H-Class ACQUITY instrument equipped with a quaternary solvent manager and a fluorescence detector. Solvent A was 50 mM ammonium formate buffer pH 4.4 and solvent B was acetonitrile. The gradient used was 0-35 min, 25-46% solvent A; 36.5-39.5 min, 100% solvent A; 43.1-55 min, 25% solvent A. The flow rate was 0.4 mL/min. The injection volume was 5 µL and the sample was prepared in 75% (v/v) acetonitrile. The fluorescence detection wavelengths were $\lambda$ex=265 nm and $\lambda$em=425 nm with a data collection rate of 20 Hz. All data was processed using Empower 3 chromatography workstation software.

Example 2: Cloning, Expression and Properties of *Omnitrophica* α-L-Fucosidase

The DNA (GenBank: LMZT01000142.1, REGION: 29928 . . . 31277) encoding *Omnitrophica* α-L-fucosidase (Gen Bank: KXK31601.1) was synthesized in vitro and DNA fragment encoding 23-449 amino acids was cloned into bacterial expression vector pJS119K using NEBuilder® HiFi DNA Assembly Cloning Kit (New England Biolabs, Ipswich, Mass.). A codon optimized DNA sequence encoding fucosidase O lacking its signal peptide (23-449 amino acids) was synthesized by Integrated DNA Technologies (Coralville, Iowa). The DNA fragment was cloned into bacterial expression vector pJS119 (Furste, et al., Gene, 48:119-131, 1986) using the NEBuilder HiFi DNA Assembly Cloning Kit.

The assembled plasmid was used for the transformation of *E. coli* expression strain (NEB® Express Competent *E. coli* (New England Biolabs, Ipswich, Mass.)). Bacterial α-L-fucosidase was expressed by induction with 0.4 mM IPTG at 30° C. for 4 hours. The cells were harvested by centrifugation and suspended in 50 mL of 20 mM Tris-HCl, pH 7.5. The cells were lysed by sonication with six 15 second bursts. Cell debris was removed by centrifugation at 19,000×g for 60 minutes at 4° C. The cleared cell lysate was applied to a 5 mL (bed volume) DEAE column (GE Healthcare Life Sciences, Marlborough, Mass.) equilibrated with 20 mM Tris-HCl, pH 7.5. Bound proteins were eluted with a 0-300 mM NaCl gradient in 20 mM Tris-HCl, pH 7.5. The fractions containing fucosidase O were pooled and ammonium sulfate was added to 1.5 M final concentration. The expressed protein purified using conventional liquid chromatography methods using hydrophobic interaction chromatography on 5 mL (bed volume) Phenyl Sepharose FF (low sub) column (GE Healthcare Life Sciences, Marlbourough, Mass.). Bound protein was eluted using a reverse gradient of 1.5-0 M ammonium sulfate in 20 mM Tris-HCl, pH 7.5. Pooled fractions containing pure protein were dialyzed against 20 mM Tris-HCl, pH 7.5 containing 50 mM NaCl, 1 mM EDTA and concentrated using Vivaspin® 20 concentrators (Sartorius Stedim Biotech, Göttingen, Germany). A synthetic substrate 2-Chloro-4-nitrophenyl α-L-fucopyranoside (CNP-Fuc) was used to assay enzymatic activity during chromatography purification. 1 µl of α-L-fucosidase sample was added to 100 µl of 2 mM CNP-Fuc in 20 mM sodium acetate buffer, pH 5.5, and incubated 1 hour at 37° C. Absorbance readings were taken at 405 nm.

Fucosidase Purity

Purified fucosidase was tested for the presence of contaminating exoglycosidase activities using fluorescent-labeled oligosaccharides and glycopeptides. Typically, fluorescent-labeled substrate (0.3 nmol) was incubated at 37° C. for 16 hours with 3 µg of fucosidase O in 10 µL of reaction buffer (50 mM sodium acetate, pH 5.5). The reaction mix was spotted onto a silica-60 thin layer chromatography (TLC) plate (EMD Millipore, Burlington, Mass.) and separated using a mobile phase of isopropanol-ethanol-water (110:50:25; v/v/v). Reaction products were visualized by UV light at 302 nm. Purified fucosidase was tested for the following activities: β-N-acetylglucosaminidase, α-N-acetylgalactosaminidase, β-N-acetylgalactosaminidase, β-galactosidase, α-galactosidase, α-neuraminidase, α-mannosidase, α-glucosidase, β-xylosidase and β-mannosidase.

Fucosidase Unit Definition and Assay

One unit of fucosidase was defined as the amount of enzyme required to cleave >95% of fucose from 1 nmol of the human IgG N-glycan GOF (GlcNAcβ1-2Manα1-6 (GlcNAcβ1-2Manα1-3)Manβ1-4GlcNAcβ1-4GlcNAc (Fucα1-6)-AMAC), in 1 hour at 37° C. in a total reaction volume of 10 μL. To assay fucosidase O, two-fold dilutions of enzyme were incubated with 1 nmol AMAC-labeled G0F substrate in 50 mM sodium acetate (pH 5.5) containing 5 mM $CaCl_2$ in a 10 μL reaction. The reaction mix was incubated at 37° C. for 1 hour. Separation of reaction products were visualized via thin layer chromatography (Wong-Madden, et al., Glycobiology, 5:19-28, 1995).

Fluorescent Labeling of Oligosaccharide Substrates

To label N-glycan substrates, 10 μL of a fluorescent labeling mix (350 mM 2-aminobenzamide (2-AB), 1 M sodium cyanoborohydride in acetic acid/dimethyl sulfoxide [30:70]) was added to each tube containing a dried N-glycan sample. The reaction was incubated at 65° C. with agitation at 700 rpm for 120 minutes. For labeling with 7-amino-4-methylcoumarin (AMC), 10 μL of a labeling mix (430 mM AMC, 1 M sodium cyanoborohydride in acetic acid/methanol [4:30]) added per 3 nmol of dried N-glycans. The reaction was incubated at 80° C. for 45 minutes. Excess label was removed by passage over HILIC SPE MacroSpin™ columns (The Nest Group, Southborough, Mass.).

Substrate Specificity and Substrate Preference of the Purified Fucosidase O

Substrate specificity of purified fucosidase O was determined using N-glycan or oligo saccharide substrates containing α(1,6)-linked fucose (M3N2F-2-AB), α(1,2)-linked fucose (2'-Fucosyllactose-AMC), α(1,3)-linked fucose (Lacto-N-fucopentose III-AMC) or α(1,4)-linked fucose (Lacto-N-fucopentose II-AMC) (see Example 1). 2 pmol of 2-AB-labeled glycan or 30 pmol AMC-labeled glycan was incubated with 0.5 μg of fucosidase O overnight at 37° C. in 50 mM sodium acetate, pH 5.5. At the end of incubation time, 100 μl of 20% acetonitrile was added to the mix to stop the reaction. The reaction mixture was transferred to the Nanosep® 10K Omega centrifugal device (Pall Corporation, Port Washington, N.Y.) and centrifuged for 5 minutes at 12,000×g. For UPLC-HILIC-FLR analysis, 5 μl of each sample was mixed with 11.7 μl acetonitrile (final ratio 30:70 water/acetonitrile). A 5-10 μl aliquot of this mix was used for UPLC-HILIC-FLR separation as described in Example 1(IV). The results (shown in FIG. 9) indicate that *Omnitrophica* fucosidase is active on α(1,6)-, α (1,2)- and α(1,4)-linked fucose, but shows no activity on α(1,3)-fucose.

The glycosidic bond preference of recombinant BKF (rBKF) (New England Biolabs, Ipswich, Mass.) and *Omnitrophica* enzymes were compared (see for example, FIG. 11). 20 pmol of 2-AB-labeled glycan or 300 pmol of AMC-labeled glycan was incubated with 1 μg of *Omnitrophica* α-L-fucosidase or 1 μg of BKF in 50 mM sodium acetate buffer, pH 5.5 in a total reaction volume of 100 μl at 37° C. At the end of each time point, 10 μl aliquot was taken and the reaction was stopped by adding 100 μl of 20% acetonitrile. The reaction mixture was transferred to the Nanosep 10K Omega centrifugal device and centrifuged for 5 minutes at 12,000×g. For UPLC-HILIC-FLR analysis, 5 μL of each sample was mixed with 11.7 μl acetonitrile (final ratio 30:70 water/acetonitrile). A 5 μL aliquot of this mix was used for UPLC-HILIC-FLR separation as described in Example 1(IV). Activity assays with results described in FIG. 9 and FIG. 11 were performed in the 50 mM sodium acetate buffer, pH 5.5

Fucosidase O exhibits highest activity on α(1,6)-linked fucose, followed by α(1,2)- and α(1,4)-fucose, whereas rBKF cleaves more efficiently α(1,2)-linked fucose than α(1,6)- and α(1,4)-fucose. This data also shows that under the conditions used the fucosidase O cleaves the core α(1,6)-fucose from 2-AB-labeled N-glycans very rapidly (within 1 hour).

Optimal pH of Fucosidase O

An activity assay was performed using 0.5 μg of purified fucosidase O and 30 pmol of 2'-Fucosyllactose-AMC substrate in buffers of varying pH values ranging from pH 7.5-pH 3.0. Following buffers were used: 50 mM glycine buffer, pH 3.0; 50 mM sodium acetate, pH 4.3; 50 mM sodium citrate, pH 4.5; 50 mM sodium acetate, pH 5.0; 50 mM MES, pH 6.0; 50 mM MES, pH 6.5; 50 mM sodium phosphate, pH 7.0; 50 mM sodium phosphate, pH 7.5. The reactions were incubated at 37° C. overnight and the samples were cleaned and analyzed by UPLC-HILIC-FLR as described in Example 1(IV). The results are shown in FIG. 10. Optimal activity was observed at a pH below 5.5 and as low as 3.0.

Example 3: Activity Assays

Fucosidase Activity Using Glycans Labeled with Fluorophore Dyes

I. Fucosidase Activity on an N-Glycans Having a α(1,6)-Core Fucose Labeled with RFMS.

Several α-L-fucosidases were tested for their ability to cleave off core fucose from the N-glycans labeled with one of the "instant" labels, RFMS (see Example 1). Labeled N-glycans (20 pmol) were incubated overnight at 37° C. in the 50 mM sodium acetate buffer, pH 5.5 with different α-L-fucosidases (1 μg of each fucosidase O, *Fibrella* fucosidase and rBKF used).

After the fucosidase reaction, N-glycans were analyzed by UPLC-HILIC-FLR (see Example 1(IV)). The results are shown in FIG. 6. Removal of the core α(1,6)-fucose from N-glycan causes a diagnostic shift in the N-glycan's chromatographic mobility (indicated by arrows). The results indicate that only fucosidase O was able to remove completely core α(1,6)-fucose from the N-glycans labeled with RFMS. Very little to no effect was observed with rBKF or with *Fibrella* fucosidase over the same time period. Also important to note that fucosidase O performed equally well on various types of core fucosylated, RFMS-labeled N-glycans (bi-antennary, containing bisecting GlcNAc, sialilated, etc.) present in the analyzed sample.

II. Fucosidase Activity on an N-Glycans Having a α(1,6)-Core Fucose Labeled with 2-AB α-L-Fucosidases were Compared for their Ability to Release Core Fucose from the N-Glycans Labeled with 2-AB Via Reductive Amination.

8 pmol of NA2F-2-AB was incubated at 37° C. in 40 μl of the 50 mM sodium acetate buffer, pH 5.5 with 0.11 μg of each native BKF, rBKF and fucosidase O. At the end of each time point (0, 1, 3, 16 hours), 10 μl aliquot was taken and the reaction was stopped by adding 100 μl of 20% acetonitrile.

Figure 7:
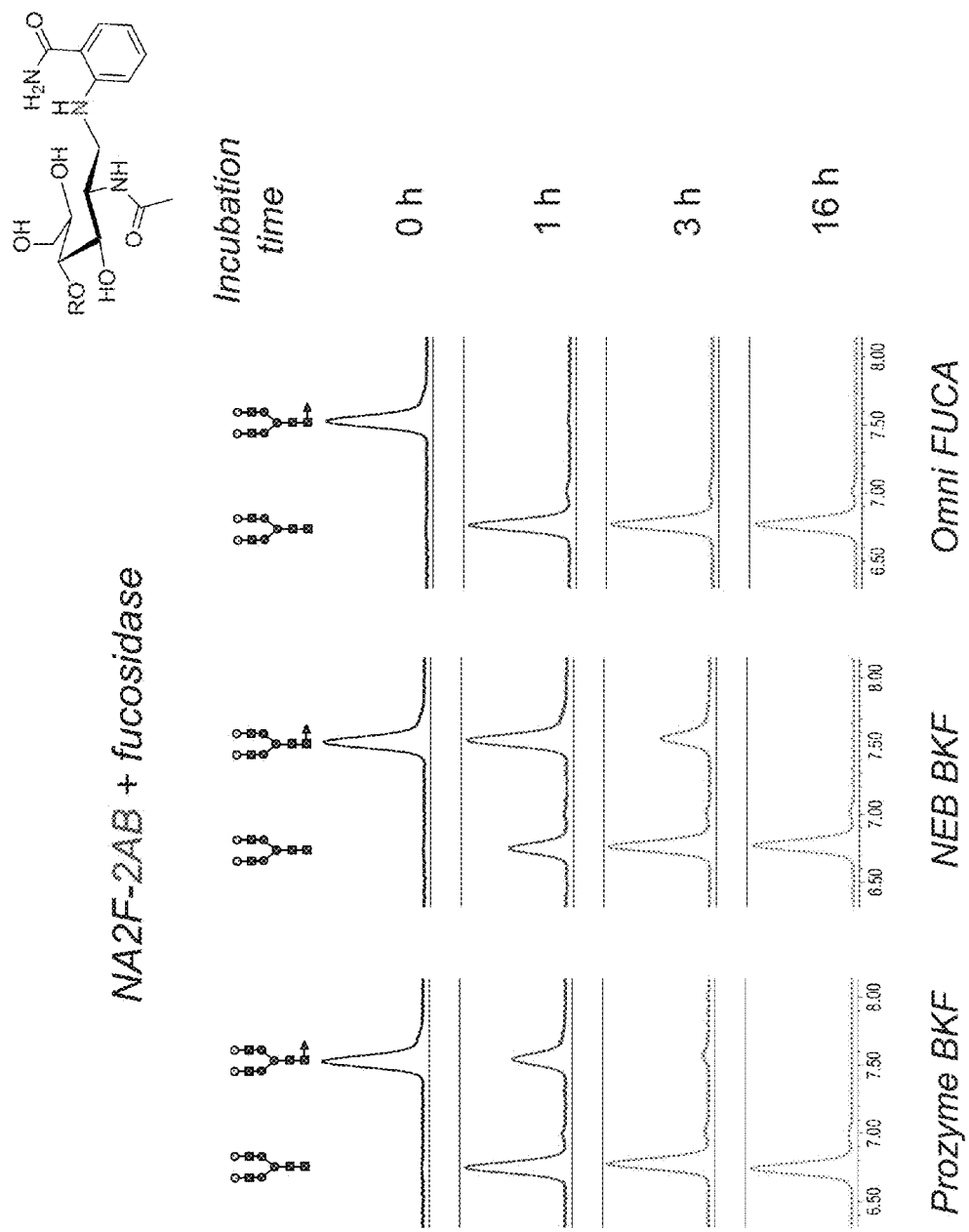
FIG. 7 shows the chromatographic profiles of a UPLC-separated N-glycan substrate (NA2F-2-AB) after treatment with equal amounts of different fucosidases over time. NA2F-2-AB has been labeled with the traditional label 2-AB via an amide bond. *Omnitrophica* fucosidase cleaves α(1,6) fucose from NA2F-2-AB rapidly (within 1 hour) while commercial BKF (Prozyme, Hayward, Calif. or New England Biolabs, Ipswich, Mass.) does not achieve complete cleavage until between 3 and 16 hours.

After the fucosidase reaction, N-glycans were analyzed by UPLC-HILIC-FLR as described in Example 1(IV). The results are shown in FIG. 7. Removal of the core α(1,6)-fucose from N-glycan causes a diagnostic shift in the N-glycan's chromatographic mobility. The data indicate the fucosidase O rapidly cleaves the core fucose from 2-AB-labeled N-glycan within 1 hour while equal amount of the commercial fucosidases do not achieve complete cleavage until more than 3 hours. Thus, under the conditions tested fucosidase O demonstrates superior performance (speed and complete removal of core fucose) on the substrates with 2-AB label.

Figure 8A:
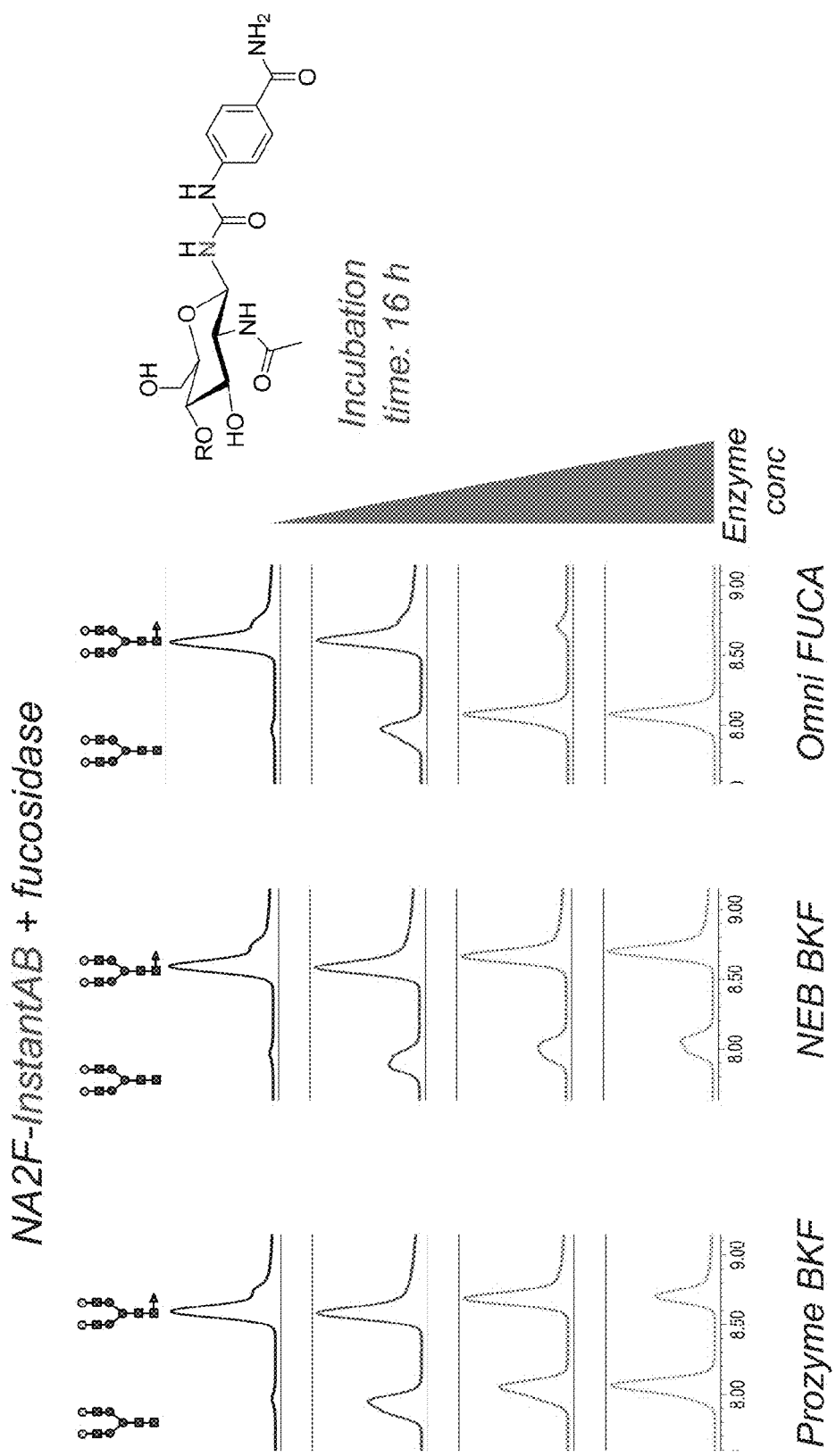
FIGS. 8A-8C shows the chromatographic profiles of UPLC-separated N-glycan substrates (NA2F) having different labels, and treatment with different fucosidases. In each panel, NA2F has been labeled with a different compound via a carbamide linkage. Increasing concentrations of *Omnitrophica* fucosidase, Prozyme BKF and New England Biolabs BKF were compared over 16 hour incubations. The structures of the substrate and product N-glycans depicted on the top of the panels.
Figure 8B:
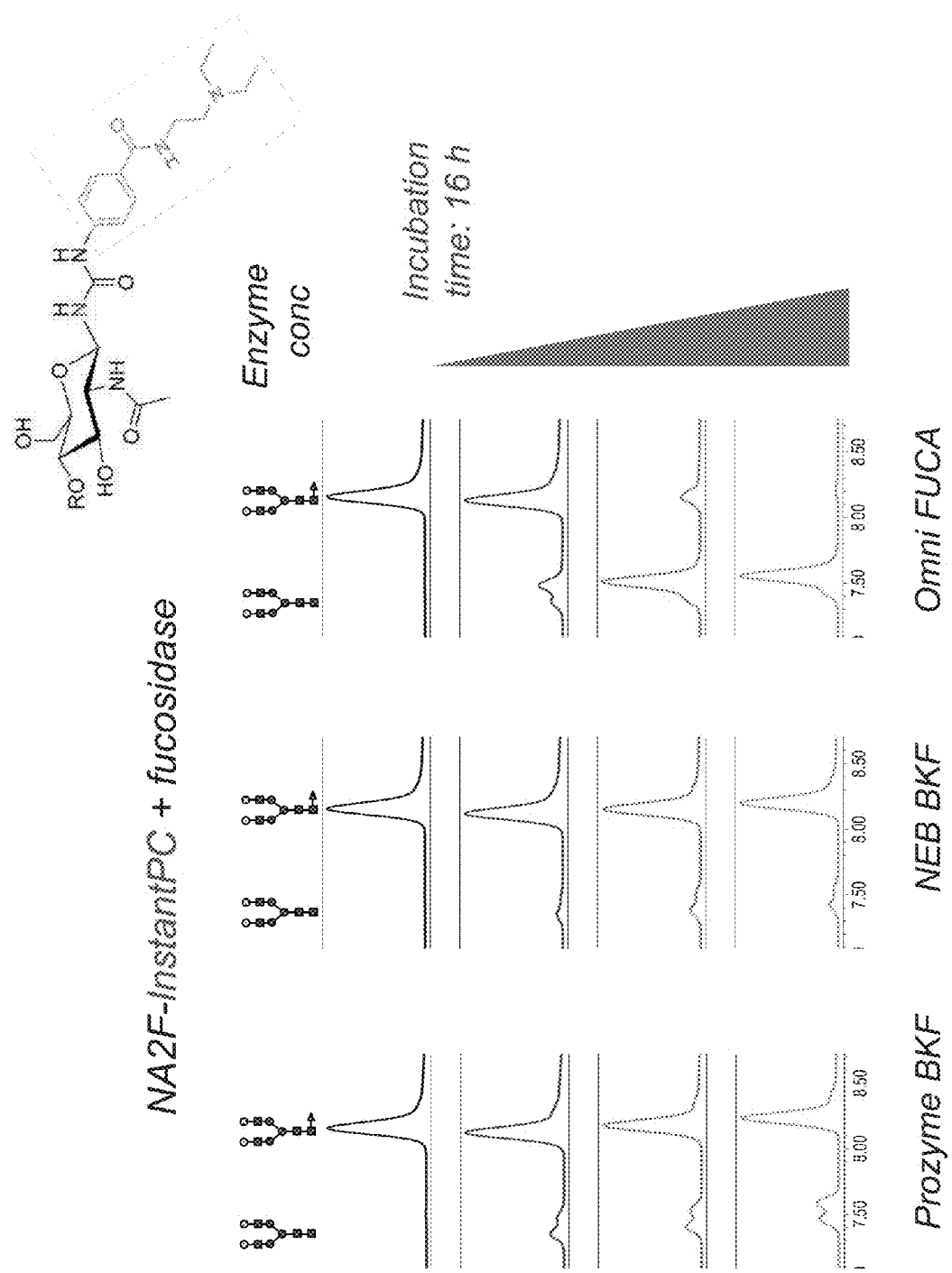
Figure 8C:
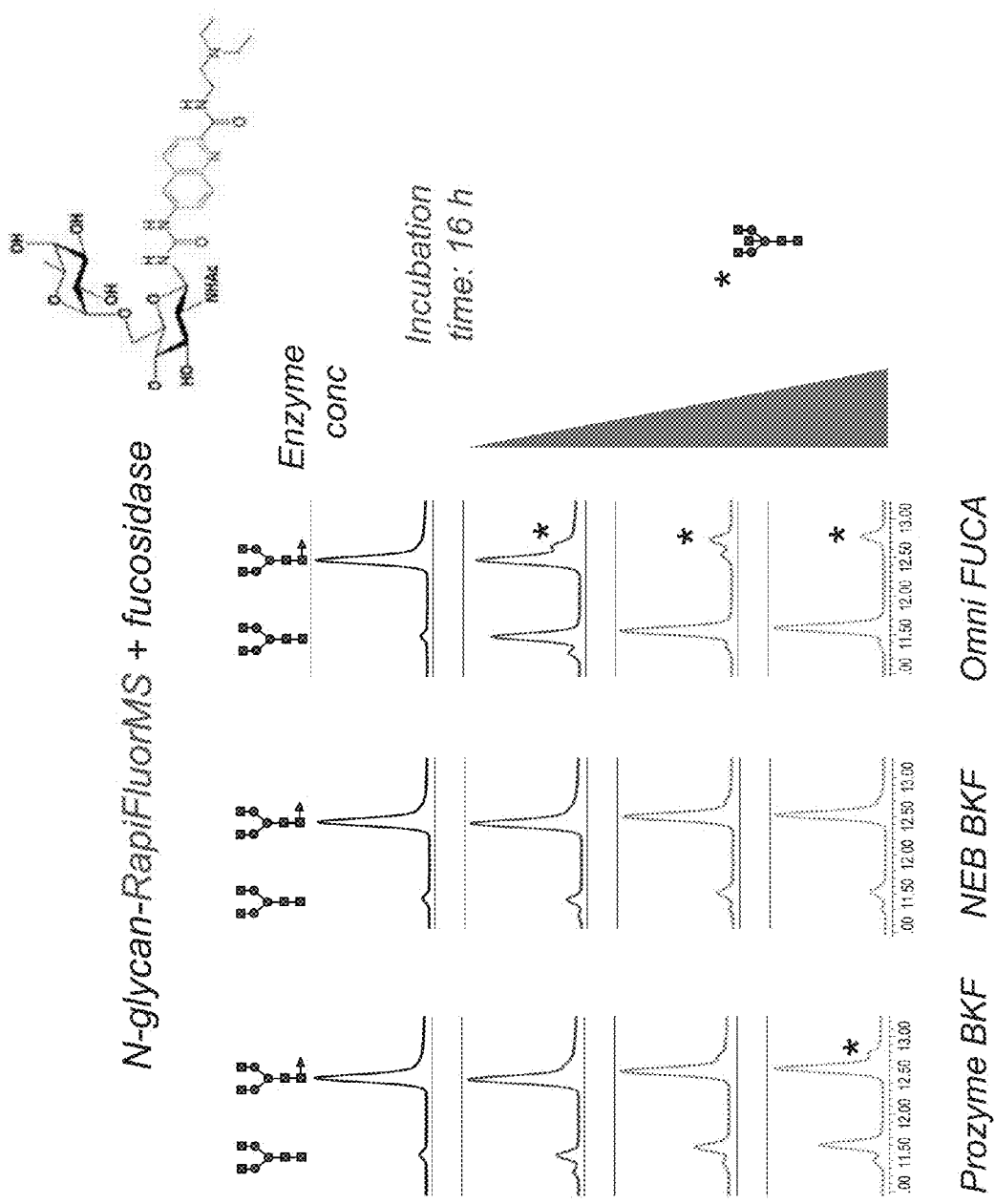

III. Fucosidase Activity on N-Glycans Having a α(1,6)-Core Fucose Labeled with InstantAB, InstantPC, RFMS Labels The release of core fucose from N-glycans labeled with different "instant" labels was tested. 2 pmol of NA2F-InstantAB or NA2F-InstantPC, or 24 pmol of human IgG N-glycans labeled with RFMS was incubated at 37° C. for 16 hours in 40 µl of the 50 mM sodium acetate buffer, pH 5.5 with increasing concentrations of each enzyme: 0, 6, 16, 30 mU of native BKF; 0, 20, 64, 120 U of rBKF and 0, 0.11, 0.8 and 2.2 µg of fucosidase O. At the end of incubation time, the reaction was stopped by adding 100 µl of 20% acetonitrile. The reaction mixture was cleaned-up using Nanosep 10K Omega centrifugal device and N-glycans were analyzed by UPLC-HILIC-FLR as described in Example 1(IV). The results are shown in FIG. 8A-8C: (FIG. 8A) InstantAB; (FIG. 8B) InstantPC; (FIG. 8C) RFMS.

The results show that, under the conditions used, efficient and complete removal of the core fucose from N-glycan with tested "instant" labels was attained only with fucosidase O while the commercial fucosidases do not achieve complete cleavage even at the highest concentrations tested. Again, this demonstrates a superior performance of fucosidase O on the substrates labeled with various "instant" labels (containing only fluorophore or fluorophore+charge tag).

Biochemical properties of Fucosidase O

To define the optimal reaction conditions for Fucosidase O, various biochemical properties of the enzyme were examined. Enzymatic activity was assessed from pH 3.0-pH 8.0 using a trimannosyl N-glycan substituted with α(1,6)-linked core fucose as a substrate. Fucosidase O was highly active from pH 4.0-pH 6.0 with optimal activity at pH 5.5. Fucosidase O was not affected by buffer containing $Mn^{2+}$, $Mg^{2+}$, $Ca^{2+}$, $Ni^{2+}$ ions but showed significantly reduced activity in buffer containing $Fe^{2+}$, $Zn^{2+}$ and $Cu^{2+}$ ions, with $Cu^{2+}$ reducing activity by 95% under the reaction conditions used. The chelating agent EDTA had no effect on fucosidase activity, indicating that metal ions were not required for catalysis. The effect of temperature on enzyme activity and stability was also tested. The enzyme exhibited optimal activity at 50° C.

Substrate Specificity of Recombinant Fucosidase O

Substrate specificity of fucosidase O was tested using various fucosylated N-glycans and other oligosaccharides as substrates. The substrates were fluorescently labeled with either 2-AB or AMC. Each oligosaccharide substrate was mixed with the enzyme and incubated for 0-48 hours. Reaction mixtures were analyzed at different incubation time points by UPLC-HILIC-FLR. For each sample, the area of individual peaks corresponding to undigested and digested substrate was obtained via integration. This permitted calculation of the percent of released fucose from each substrate. Complete digestion of α(1,6)-linked core fucose was observed with NA2F (an asialo-, galactosylated biantennary complex N-glycan with core fucose) (FIG. 16A). Terminal α(1,2)-linked fucose was also completely removed from 2-fucosyllactose (FIG. 16B). However, even after an extended 48 hour incubation, only 7% of α(1,4)-linked fucose was released from lacto-N-fucopentaose II (FIG. 16C), and no hydrolysis of α(1,3)-linked fucose was observed using lacto-N-fucopentaose III as a substrate (FIG. 16D).

The linkage preference of recombinant Fucosidase O was compared to that of native BKF using fucosylated oligosaccharide substrates containing α(1,2)-linked fucose (2'-fucosyllactose) and α(1,6)-linked fucose (NA2F). After a 1 hour incubation, fucosidase O released α(1,6) and α(1,2)-linked fucose with 95% and 27% efficiency, respectively; while BKF released 33% of α(1,6)-linked fucose and 100% of α(1,2)-linked fucose (FIGS. 16A and 16B, dotted lines). After 18 hour incubation, both α(1,6), α(1,2)-linked fucose substrates were completely hydrolyzed by both enzymes (FIGS. 16A and 16B). Therefore, fucosidase O showed a marked preference for α(1,6)-linked core fucose (α(1,6>1, 2), whereas BKF preferred α(1,2)-linked fucose (α(1,2>1, 6).

Core α(1,6) Fucose Removal from N-glycans Containing Urea-Linked Dyes

The efficiency of hydrolysis of α(1,6)-linked core fucose from an RFMS-labeled N-glycan (NGA2F) by BKF and fucosidase O was evaluated. Complete defucosylation of RFMS-labeled NGA2F was observed after treatment with fucosidase O (35 U/mL) for 16 hours at TEMP (FIG. 17). In comparison, digestion with BKF (2 U/mL) resulted in a release of only ~61% core fucose from RFMS-labeled N-glycan (FIG. 17). To expand on this observation, we also tested the ability of fucosidase O and BKF to remove core fucose from the N-glycan NA2F labeled with the urea-linked aminobenzamide dyes (InstantAB and InstantPC). This experiment was performed by incubating NA2F-InstantAB or NA2F-InstantPC with fucosidase O (35 U/mL) or BKF (2 U/mL) for 16 hours at 37° C. BKF was able to remove 90% of core fucose from NA2F-InstantAB and only 49% from NA2F-InstantPC, whereas >99% of core fucose was released from both substrates by Fucosidase O (FIG. 17). These data illustrate that in addition to urea-linked aminoquinoline dyes, BKF can also be inhibited by urea-linked aminobenzamide dyes. In contrast, fucosidase O appears to efficiently remove core fucose in the presence of any of the existing urea-linked dyes.

Example 4: Enzymatic Release of α(1,6)-Linked Core Fucose from Complex N-glycans Attached to Glycoproteins Anti-MBP monoclonal antibody (murine IgG2a) was incubated with fucosidase O to investigate if this fucosidase could liberate α(1,6)-linked core fucose from glycoprotein under non-denaturing conditions.

After fucosidase treatment, N-glycans were released from protein using PNGase F, labeled with 2-AB and analyzed by UPLC-HILIC-FLR. The results presented in FIG. 15A-15B show that fucosidase O can liberate α(1,6)-linked core fucose from the complex N-glycans which are covalently attached to glycoprotein at asparagine residues by an N-glycosidic bond.

More specifically, 15 µg of native murine anti-MBP antibody (New England Biolabs, Ipswich, Mass.) were mixed with 6.5 µg of α-L-fucosidase in 50 mM sodium acetate buffer, pH 6.0 in a 20 µl final reaction volume, and the reaction mixes were incubated at 37° C. for 36 hours. After the treatment, the reactions were stopped, diluted with 90 µl of water and the buffer exchanged to 50 mM sodium phosphate, pH 7.5 using Nanosep 10K Omega centrifugal devices (Pall Life Sciences, Port Washington, N.Y.). 2.5 µl of PNGase F was added to the filters and incubated at 37° C.

for 1.5 hours. The released glycans were collected by centrifugation, dried, labeled with 2-AB and cleaned-up as described in Example 1(II-III). The purified labeled glycans were further analyzed by UPLC-HILIC-FLR as described in Example 1(IV). Using this approach, different core fucosylated glycoproteins can be remodeled using fucosidase O.

Core α(1,6) Fucose Removal from Serum IgG N-glycans Labeled with RFMS

Fucosidase O was tested for its ability to liberate core fucose from RFMS-labeled N-glycans in a complex sample. Human IgG harbors a mixture of many complex N-glycan structures, the vast majority of which are α(1,6) core fucosylated (Stockmann, 2015; Vainauskas, et al., Sci Rep., 6:34195, 2016). In this experiment, an RFMS-labeled human IgG N-glycan mixture was used as a substrate (FIG. 18A). Significantly higher concentrations of fucosidase O (~23 fold, 35 U/mL) and extended incubation time (16 hours) at 37° C. were required to achieve complete digestion of RFMS-labeled glycans (FIG. 18B). For comparison, a 16-hour reaction using a proportionally higher concentration of BKF (2 U/mL) showed only partial digestion and resulted in an increase in the sample's complexity (FIG. 18C). Furthermore, increasing the amount of BKF in the reaction mixture to 5 U/mL and the length of digestion to 24 hours did not result in complete digestion. This is consistent with the previously reported observation that RFMS hinders removal of core fucose by BKF (O'Flaherty, et al., J Proteome Res. 16:4237-4234, 2017).

It will also be recognized by those skilled in the art that, while the invention has been described above in terms of preferred embodiments, it is not limited thereto. Various features and aspects of the above described invention may be used individually or jointly. Further, although the invention has been described in the context of its implementation in a particular environment, and for particular applications those skilled in the art will recognize that its usefulness is not limited thereto and that the present invention can be beneficially utilized in any number of environments and implementations where it is desirable to examine analytes. Accordingly, the claims set forth below should be construed in view of the full breadth and spirit of the invention as disclosed herein.

What is claimed is:

1. A reaction mix comprising:
   (a) an α-L-fucosidase comprising an amino acid sequence that is identical to amino acids 23-359 of the sequence of SEQ ID NO:1; and
   (b) a conjugate comprising an N-glycan and a label that are joined by an carbamide bond.

2. The reaction mix of claim 1, wherein the label comprises a fluorophore and/or a charge tag.

3. The reaction mix of claim 1, wherein the N-glycan of the conjugate comprises a core fucose.

4. The reaction mix of claim 1, wherein the N-glycan is linked to the label via the reducing end of the N-glycan.

5. The reaction mix of claim 1, wherein the N-glycan is from a therapeutic glycoprotein.

6. The reaction mix of claim 1, wherein the reaction mix further comprises:
   (c) one or more exoglycosidases selected from the group consisting of:
      α2-3 neuraminidase S;
      α2-3,6,8,9 neuraminidase A;
      α1-3,4,6 galactosidase;
      β1-4 galactosidase;
      β-N-acetylglucosaminidase S; and
      α1-2,3,6 mannosidase.

7. The reaction mix of claim 1, wherein the reaction mix has a pH in the range of pH 3.0 to pH 5.5.

8. An enzyme mix comprising:
   (a) an α-fucosidase comprising an amino acid sequence that is identical to amino acids 23-359 of the sequence of SEQ ID NO:1; and
   (b) one or more exoglycosidases that are not encoded by the genome of *Omnitrophica*, selected from the group consisting of:
      α2-3 neuraminidase S;
      α2-3,6,8,9 neuraminidase A;
      α1-3,4,6 galactosidase;
      β1-4 galactosidase;
      β-N-acetylglucosaminidase S; and
      α1-2,3,6 mannosidase.

9. The enzyme mix according to claim 8, wherein none of the one or more exoglycosidases in the enzyme mix is glycosylated.

10. The enzyme mix of claim 8, wherein the enzyme mix comprises two or more of the exoglycosidases.

11. The enzyme mix of claim 8, wherein the enzyme mix comprises three or more of the exoglycosidases.

12. The enzyme mix of claim 8, wherein the enzyme mix comprises α2-3 neuraminidase S, α2-3,6,8,9 neuraminidase A, α1-3,4,6 galactosidase, β1-4 galactosidase and β-N-acetylglucosaminidase S.

13. A kit, comprising:
   a. an α-fucosidase comprising an amino acid sequence that is identical to amino acids 23-269 of the sequence of SEQ ID NO:1; and
   b. a label comprising a reactive carbamate.

14. The kit of claim 13, wherein the kit further comprises peptide:N-glycosidase F (PNGase F).

15. The kit of claim 13, further comprising one or more exoglycosidases selected from the group consisting of:
   α2-3 neuraminidase S;
   α2-3,6,8,9 neuraminidase A;
   α1-3,4,6 galactosidase;
   β1-4 galactosidase;
   β-N-acetylglucosaminidase S; and
   α1-2,3,6 mannosidase.

16. The kit of claim 15, wherein at least one of the one or more exoglycosidases is combined with the α-fucosidase in a reaction mixture.

17. The kit of claim 13, wherein the label comprises a fluorophore and/or a charge tag.

* * * * *